(12) United States Patent
Dodda et al.

(10) Patent No.: US 10,327,448 B2
(45) Date of Patent: Jun. 25, 2019

(54) **BACTERIUM OF *BACILLUS* GENUS AND USES THEREOF**

(71) Applicant: DCM Shriram Ltd., New Delhi (IN)

(72) Inventors: Santosh Kumar Dodda, Hyderabad (IN); Dwarkesh Singh Parihar, Hyderabad (IN); Paresh Kumar Verma, Hyderabad (IN)

(73) Assignee: DCM Shriram Ltd., New Delhi (IN)

( * ) Notice: Subject to any disclaimer, the term of this patent is extended or adjusted under 35 U.S.C. 154(b) by 118 days.

(21) Appl. No.: 15/503,941

(22) PCT Filed: Jul. 21, 2015

(86) PCT No.: PCT/IN2015/000294
§ 371 (c)(1),
(2) Date: Feb. 14, 2017

(87) PCT Pub. No.: WO2016/027279
PCT Pub. Date: Feb. 25, 2016

(65) Prior Publication Data
US 2017/0231230 A1    Aug. 17, 2017

(30) Foreign Application Priority Data

Aug. 16, 2014 (IN) .......................... 2331/DEL/2014

(51) Int. Cl.
*A01N 63/00* (2006.01)
*C12R 1/125* (2006.01)
*A01N 63/02* (2006.01)
*C12N 1/20* (2006.01)

(52) U.S. Cl.
CPC ............ *A01N 63/00* (2013.01); *A01N 63/02* (2013.01); *C12N 1/20* (2013.01); *C12R 1/125* (2013.01)

(58) Field of Classification Search
None
See application file for complete search history.

(56) References Cited

U.S. PATENT DOCUMENTS

2003/0082792 A1    5/2003    Bergstrom et al.

FOREIGN PATENT DOCUMENTS

| EP | 0 981 540 B1 | 7/2006 |
| KR | 20110075132 A | 7/2011 |
| WO | WO 99/09819 | 3/1999 |
| WO | WO 2000/015761 | 3/2000 |
| WO | WO 2009/031874 A1 | 3/2009 |

OTHER PUBLICATIONS

Johnson et al (Science, 102:376-377, 1945).*

Compant, S., et al., "Use of Plant Growth-Promoting Bacteria for Biocontrol of Plant Diseases: Principles, Mechanisms of Action, and Future Prospects", *Applied and Environmental Microbiology*, 71(9): 4951-4959 (Sep. 2005).
Hoffmann, W.A., et al., "Avoiding Bias in Calculations of Relative Growth Rate", *Annals of Botany*, 80: 37-42 (2002).
International Search Report and Written Opinion of the International Searching Authority for International Application No. PCT/IN2015/000294; dated Nov. 12, 2015; entitled: "Novel Bacterium of Bacillus Genus and Uses Thereof".
Li, J., et al., "Purification and characterization of a novel antifungal protein from *Bacillus subtilis* strain B29", *Journal of Zhejiang University Science B*, 10(4): 264-272 (2009).
Malusa, E., "Technologies for Beneficial Microorganisms Inocula Used as Biofertilizers" *The Scientific World Journal*, vol. 2012, Article ID 491206, 12 pgs (Nov. 2011).
Mena-Violante, H.G., et al., "Alteration of tomato fruit quality by root inoculation with plant growth-promoting rhizobacteria (PGPR): *Bacillus subtilis* BEB-13bs", *Scientia Horticulturae*, 113 (2007) 103-106.
Mohan Kumar, S.P., et al., "Development of seed coating formulation using consortium of *Bacillus subtilis* OTPB1 and *Trihoderma harzianum* OTPB3 for plant growth promotion and induction of systemic resistance in field and horticultural crops", *Indian Phytopath*, 68(1): 25-31 (2015).
Mohiddin, F.A., et al., "Tolerance of fungal and bacterial biocontrol agents to six pesticides commonly sued in the control of soil born plant pathogens", *Global Science Research Journals*, 1(1): 001-004 (Nov. 2013).
Nakamura, L.K., "Taxonomic Relationship of Black-Pigmented *Bacillus subtilis* Strains and a Proposal for *Bacillus atrophaeus* sp. nov.", *International Journal of Systematic Bacteriology*, Jul. 1989), 39(3): 295-300 (Jul. 1989).
Travers, R.S., et al., "Selective Process for Efficient Isolation of Soil *Bacillus* spp." *Applied and Environmental Microbiology*, 53(6): 1263-1266 (Jun. 1987).
Notification Concerning Transmittal of International Preliminary Report on Patentability for International Application No. PCT_IN2015_000294, Novel Bacterium of Bacillus Genus and Uses Thereof, dated Mar. 2, 2017.

* cited by examiner

*Primary Examiner* — Brian Gangle
(74) *Attorney, Agent, or Firm* — Hamilton, Brook, Smith & Reynolds, P.C.

(57) ABSTRACT

The present work relates to a novel microbe belonging to *Bacillus* family exhibiting antimicrobial and/or antifungal and plant growth promoting activity. The present work relates to the method of its isolation and identifying extract of the novel microbe exhibiting antimicrobial and/or antifungal, plant growth promoting proteolytic amylolytie activities. In particular, there is provided a novel bacterium *Bacillus subtilis* ssp. *shriramensis* having accession number MTCC-5674. The novel bacterium is cultured in the medium to mass produce the antimicrobial and/or antifungal and plant growth promoting agent by the novel microbe and Sin the culture medium. There is provided a composition comprising the novel bacterium or an extract of the novel bacterium, which is agriculturally and pharmaceutically effective. The novel bacterium of the present work is used in the treatment against various pathogenic fungi and/or bacteria and promoting growth plants.

13 Claims, 17 Drawing Sheets

BACTERIUM OF *BACILLUS* GENUS AND USES THEREOF

Figure 1:
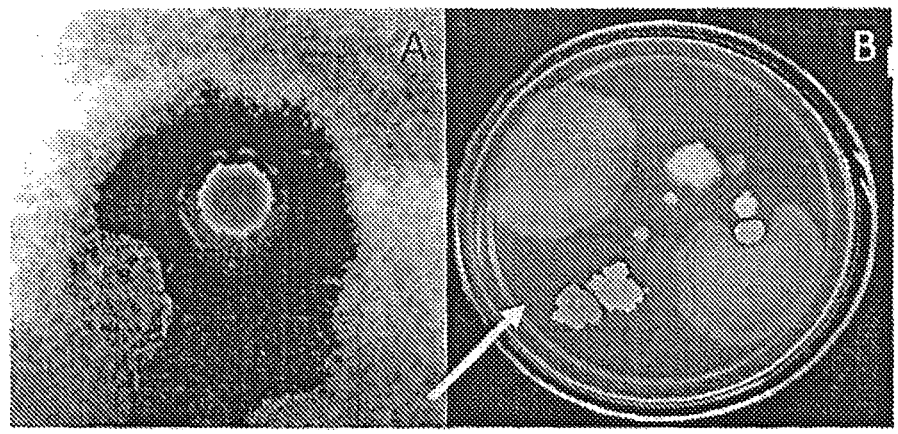

This application is the U.S. National Stage of International Application No. PCT/IN2015/000294, file Jul. 21, 2015, which designates the U.S., publication in English, and claims priority under 35 U.S.C. §§ 119 or 365(c) to Indian Application No. 2331/DEL/2014, filed Aug. 16, 2014. The entire teachings of the above applications are incorporated herein by reference.

The present invention relates to a novel bacterium belonging to *Bacillus* family, designated as *Bacillus subtilis* ssp. *shriramensis* exhibiting anti-microbial and/or anti-fungal and plant growth promoting activity, isolation and identification of extract of the novel microbe exhibiting antimicrobial and/or antifungal, proteolytic, amylolytic activities, composition comprising the novel bacterium and/or extract, method of inhibiting the growth of pathogenic microbes and/or fungi by contacting the pathogenic microbes and/or fungi with an effective amount of the novel bacterium and/or an antimicrobial and/or antifungal and plant growth promotion composition and/or agent and use thereof.

BACKGROUND OF THE INVENTION

The Earth's atmosphere is known to team with airborne microorganisms, though the high light intensities, extreme temperature variations, low concentrations of organic matter and scarcity of water, make the environment unsuitable for microbial growth. Biological material may contribute about 20%, 22% and 10% to the total airborne particulate matter by volume in remote continental, populated continental and remote maritime environments, respectively. Most of them originate from natural sources such as soil, lakes, animals and humans. Moreover, agricultural practices, health care units and industrial operations such as sewage treatment, animal rearing, fermentation processes, and food processing plants also emit viable microorganisms into the environment.

Bacteria form a large domain of single-celled, prokaryotic microorganisms. Typically a few micrometres in length, bacteria have a wide range of shapes, ranging from cocci to rods and spirals. Bacteria are ubiquitous on Earth, growing in soil, acidic hot springs, radioactive waste, water, and deep in the Earth's crust, as well as in organic matter and the live bodies of plants and animals. The bacilli are rod-shaped, gram-positive, sporulating, aerobic or facultative anaerobic bacteria. Most bacilli are saprophytes. Each bacterium creates only one spore, which is resistant to heat, cold, radiation, desiccation, and disinfectants. The bacilli exhibit an array of physiological abilities that allow them to live in a wide range of habitats, including many extreme habitats such as the desert sands, hot springs, and Arctic soils. *Bacillus* species can be thermophilic, psychrophilic, acidophilus, alkaliphilic, halotolerant, or halophilic and are capable of growing at various pH values, temperatures, and salt concentrations.

Production of antimicrobial agents seems to be a general phenomenon for most bacteria. These bacteria produce an admirable array of microbial defense systems, including broad-spectrum classical antibiotics, metabolic by-products such as organic acids, and lytic agents such as lysozyme. In addition, several types of protein exotoxins, and bacteriocins, which are biologically active peptide moieties with bactericidal mode of action, are also produced. The biological arsenal from microbes is remarkable in its diversity and natural abundance.

The search for new antimicrobial agents is a field of utmost importance. The development of resistance to antimicrobial agents is increasing at an alarming rate. Current solutions involve development of a more rational approach to antibiotic use and discovery of new antimicrobials.

Highly Relevant Patents
1. Novel bacterial strains and methods of controlling fungal pathogens (WO/2000/015761).

OBJECTIVES OF THE INVENTION

The objective of the present invention is to provide a novel bacterium exhibiting antimicrobial and/or antifungal and plant growth promotion activity.

The objective of the present invention is to isolate & identify an extract of the novel bacterium, wherein the extract displays antimicrobial and/or antifungal plant growth promotion activity.

The objective of the present invention is also to provide an antimicrobial and/or antifungal and plant growth promotion composition or agent wherein the composition or the agent comprises the novel bacterium and/or the extract of the novel bacterium.

Another objective of the present invention is to provide a method of inhibiting the growth of pathogenic microbes and/or fungi by contacting the pathogenic microbes and/or fungi with an effective amount of the novel bacterium and/or an antimicrobial and/or antifungal and plant growth promotion composition and/or agent wherein the composition or the agent comprises the novel bacterium and/or the extract of the novel bacterium and/or a mixture of the novel bacterium and its extract.

The other objective of the present invention is to provide use of the novel bacterium, an antimicrobial and/or antifungal composition or agent wherein the composition or the agent comprises the novel bacterium and/or the extract of the novel bacterium and/or a mixture of the novel bacterium and its extract, for inhibiting the growth of pathogenic microbes and/or fungi.

SUMMARY OF THE INVENTION

An aspect of the present invention is to provide an isolated, novel bacterium which is useful in producing antimicrobial and/or antifungal metabolites or agents.

One aspect of the present invention is to provide a novel form of bacterium belonging to *Bacillus* species which is designated as *Bacillus subtilis* ssp. *shriramensis* having accession number (MTCC-5674). In particular, the novel bacterium disclosed in the present work is capable of exhibiting distinct antimicrobial and/or antifungal and plant growth promotion property.

Another aspect of the present invention is to provide a process for the production of an antimicrobial and/or antifungal and plant growth promotion composition or agent wherein the composition or the agent comprises *Bacillus subtilis* ssp. *shriramensis* (MTCC-5674) and/or the extract of the *Bacillus subtilis* ssp. *shriramensis* (MTCC-5674).

There is provided a composition comprising *Bacillus subtilis* ssp. *shriramensis* (MTCC-5674). The composition may further comprise pharmaceutically acceptable excipients, diluents and/or carriers.

There is provided a composition containing an extract of *Bacillus subtilis* ssp. *shriramensis* (MTCC-5674). There is also provided a composition comprising an aqueous extract of *Bacillus subtilis* ssp. *shriramensis* (MTCC-5674). The composition may further comprise pharmaceutically acceptable excipients, diluents and/or carriers.

There is provided a method for inhibiting the growth of pathogenic microbes and/or fungi by contacting the pathogenic microbes and/or fungi with an effective amount of *Bacillus subtilis* ssp. *shriramensis* (MTCC-5674) or the extract of *Bacillus subtilis* ssp. *shriramensis* (MTCC-5674). The *Bacillus subtilis* ssp. *shriramensis* (MTCC-5674) and/or the extract of *Bacillus subtilis* ssp. *shriramensis* (MTCC-5674) may optionally contain one or more additional antimicrobial and/or antifungal and plant growth promoting agents.

There is provided in the present invention the use of *Bacillus subtilis* ssp. *shriramensis* (MTCC-5674) and/or the extract of the *Bacillus subtilis* ssp. *shriramensis* (MTCC-5674) in the formulation of an antimicrobial and/or antifungal and plant growth promotion composition or agent for inhibiting the growth of pathogenic microbes and/or fungi.

DETAILED DESCRIPTION OF THE INVENTION

The present invention provides a novel microbe belonging to *Bacillus* family designated as *Bacillus subtilis* ssp. *shriramensis* and having an accession number (MTCC-5674) and a method of producing an antimicrobial and/or antifungal and plant growth promotion composition or agent wherein the composition or the agent comprises *Bacillus subtilis* ssp. *shriramensis* (MTCC-5674) and/or the extract of the *Bacillus subtilis* ssp. *shriramensis* (MTCC-5674).

The present invention also provides a method of inhibiting the pathogenic microbes and/or fungi by contacting the microbes and/or fungi with an effective amount of the novel bacterium, *Bacillus subtilis* ssp. *shriramensis* (MTCC-5674) and/or the composition comprising the novel bacterium or its extract.

The present invention also provides use of *Bacillus subtilis* ssp. *shriramensis* (MTCC-5674), and/or an antimicrobial and/or antifungal and plant growth promotion composition or agent comprising the novel bacterium *Bacillus subtilis* ssp, *shriramensis* (MTCC-5674) and/or the extract of the *Bacillus subtilis* ssp. *shriramensis* (MTCC-5674) for inhibiting the pathogenic microbes and/or fungi.

The novel *Bacillus subtilis* ssp. *shriramensis* (MTCC-5674) may be utilized for the mass production of antimicrobial and/or antifungal and plant growth promotion composition/preparation/agent by culturing *Bacillus subtilis* ssp. *shriramensis* in the suitable growth medium under favourable conditions.

Through deep and careful researches, the inventors have surprisingly found, isolated and cultured a novel bacterium, which can produce a novel agent. Through detailed experimental researches, the inventors have also invented a method of producing the said novel agent from the said novel microorganism.

BRIEF DESCRIPTION OF ACCOMPANYING DRAWINGS

FIG. 1—Plate showing isolation and purification of *Bacillus subtilis* ssp. *shriramensis* (MTCC-5674) (A) Mother culture plate showing bacterial growth along with fungal mycelium; (B) Purification of *Bacillus subtilis* ssp. *shriramensis* (MTCC-5674) from bacterial colony(s) in (A). Arrow indicates putative bacterial colony.

Figure 2:
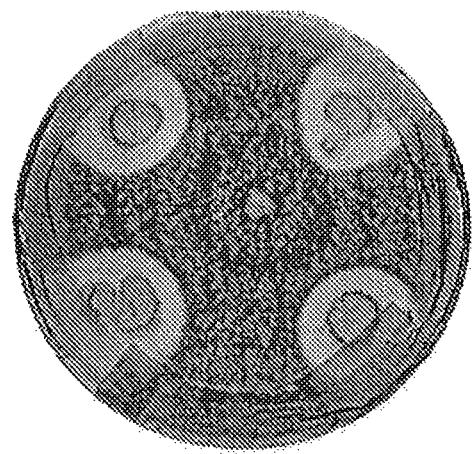

FIG. 2—Clone of one of the purified colonies of *Bacillus subtilis* ssp. *shriramensis* (MTCC-5674) showing inhibition of growth of *Fusarium oxysporum* mycelium.

Figure 3:
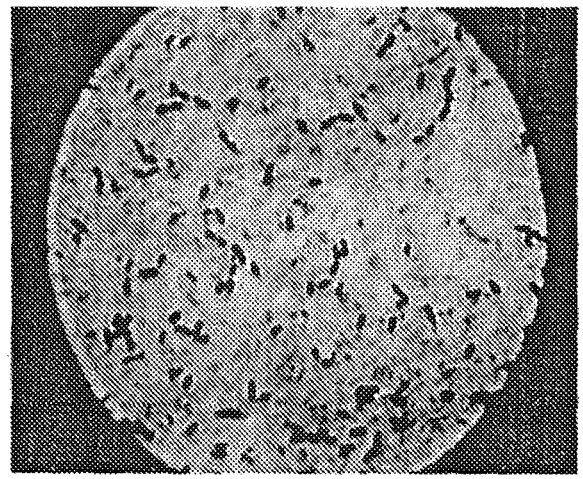

FIG. 3—Microscopic picture of vegetative bacterial cells of *Bacillus subtilis* ssp. *shriramensis* (MTCC-5674) along with spores.

Figure 4:
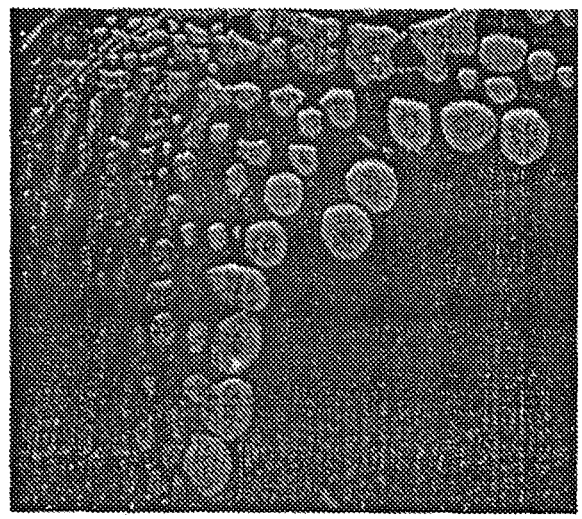

FIG. 4—Plate showing actively growing colonies of *Bacillus subtilis* ssp. *shriramensis* (MTCC-5674).

Figure 5:
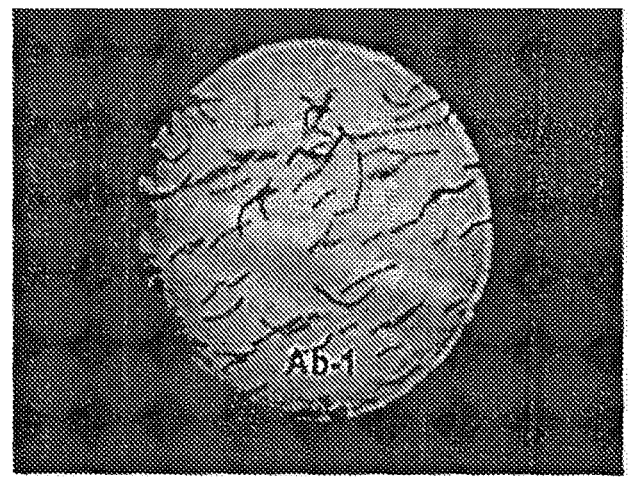

FIG. 5—Rod shaped *Bacillus subtilis* ssp. *shriramensis* (MTCC-5674) under light microscope.

Figure 6:
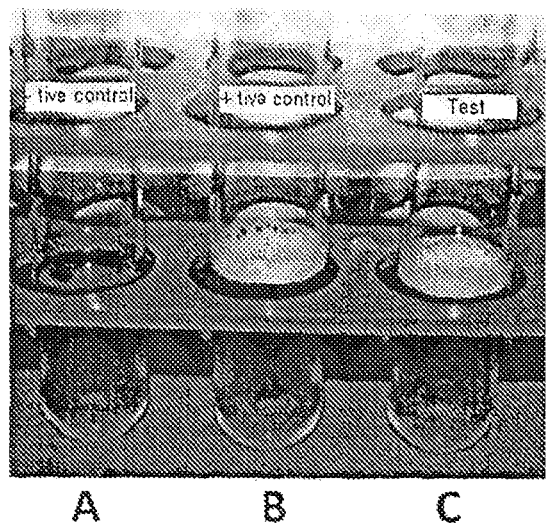

FIG. 6—Picture showing results of catalase test; (A) Negative control; (B) Positive control and (C) *Bacillus subtilis* ssp. *shriramensis* (MTCC-5674) showing positive results for catalase activity.

Figure 7:
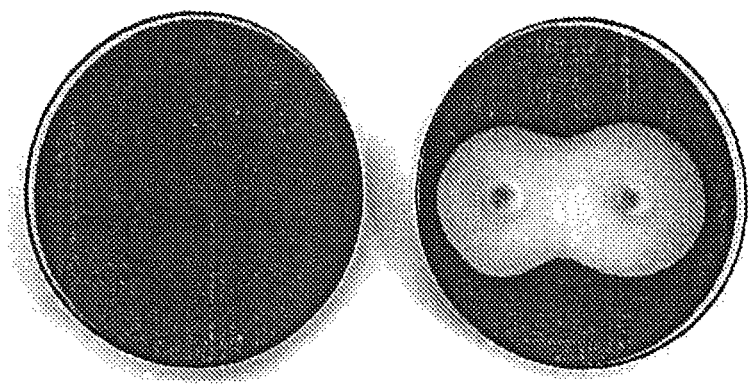

FIG. 7—Plate showing amylolytic activity of *Bacillus subtilis* ssp. *shriramensis* (MTCC-5674) culture filtrate.

Figure 8:
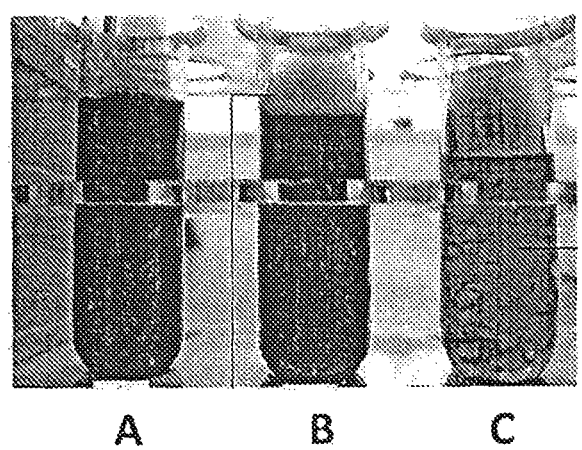

FIG. 8—Picture showing results of O/F (Oxidation-Fermentation) test (A) Negative control; (B) *Bacillus subtilis* ssp. *shriramensis* (MTCC-5674) showing color change only at the top portion of the medium; (C) Positive control.

Figure 9:
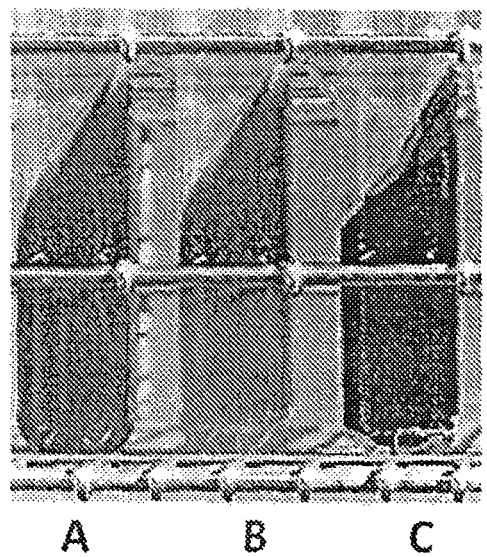

FIG. 9—Picture showing results of Hydrogen sulphide production test (A) Negative control; (B) *Bacillus subtilis* ssp. *shriramensis* (MTCC-5674) and (C) Positive control.

Figure 10:
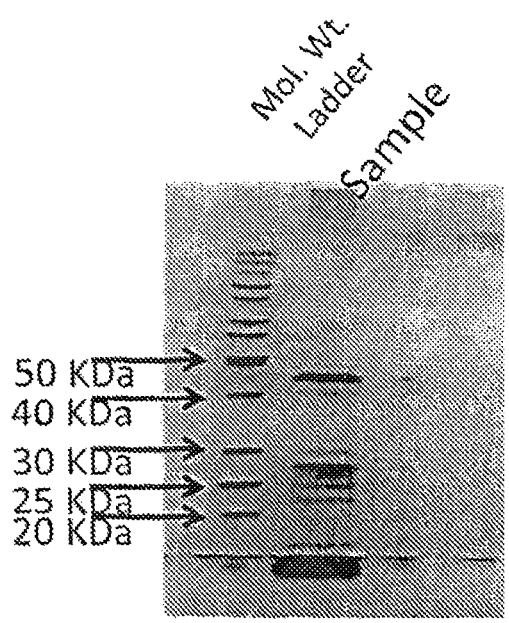

FIG. 10—Picture showing results of SDS-PAGE of the concentrated culture filtrate of *Bacillus subtilis* ssp. *shriramensis* (MTCC-5674).

Figure 11:
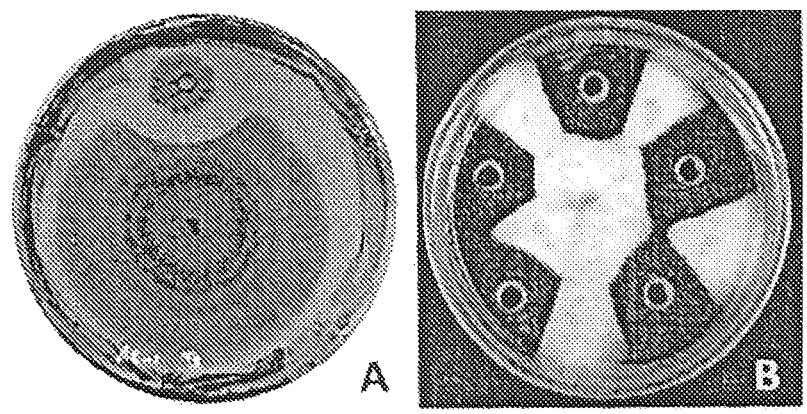

FIG. 11—Culture plates showing antimicrobial and/or antifungal activity displayed by (A) *Bacillus subtilis* ssp. *shriramensis* (MTCC-5674) colony and (B) *Bacillus subtilis* ssp. *shriramensis* (MTCC-5674) culture filtrate. *Fusarium oxysporum* culture was used as test fungus.

Figure 12:
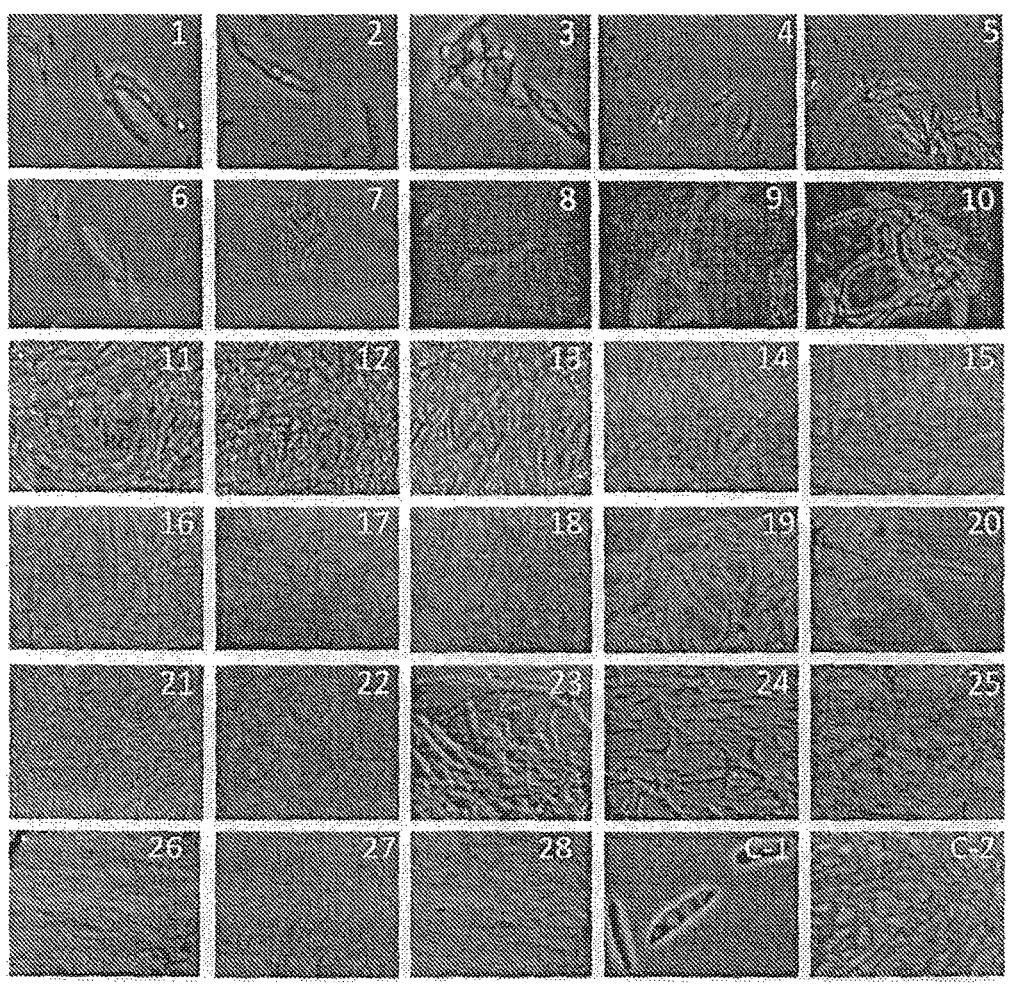

FIG. 12—Picture showing results of MIC assay of antimicrobial and/or antifungal compound by the tube dilution method 1 to C-2: Pictures of *Fusarium oxysporum* spores (observed under light microscope), after incubating in PDB containing different concentrations of antimicrobial and/or antifungal agent. 1-28 (Dilutions 1:1 to 1:100), C-1—Spores in antimicrobial and/or antifungal agent (Crude); C-2—Control (Spores in PDB broth without antimicrobial and/or antifungal agent).

Figure 13:
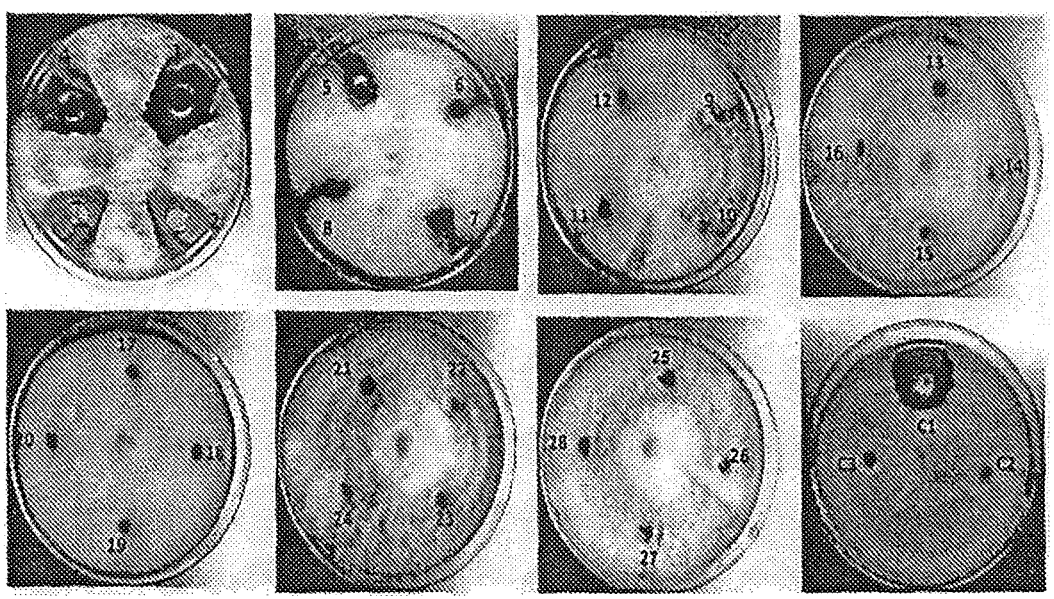

FIG. 13—Picture showing results of MIC assay of antimicrobial and/or antifungal agent by agar diffusion method. 1 to C-2: Pictures of *Fusarium oxysporum* mycelium growing on test plates. 1-28 Dilutions of antimicrobial and/or antifungal agent at 1:1 to 1:100 (v/v), C1—Well containing antimicrobial and/or antifungal agent (Crude); C2—Control well containing PDB; C3—Control well containing 70% saturated ammonium sulfate.

Figure 14:
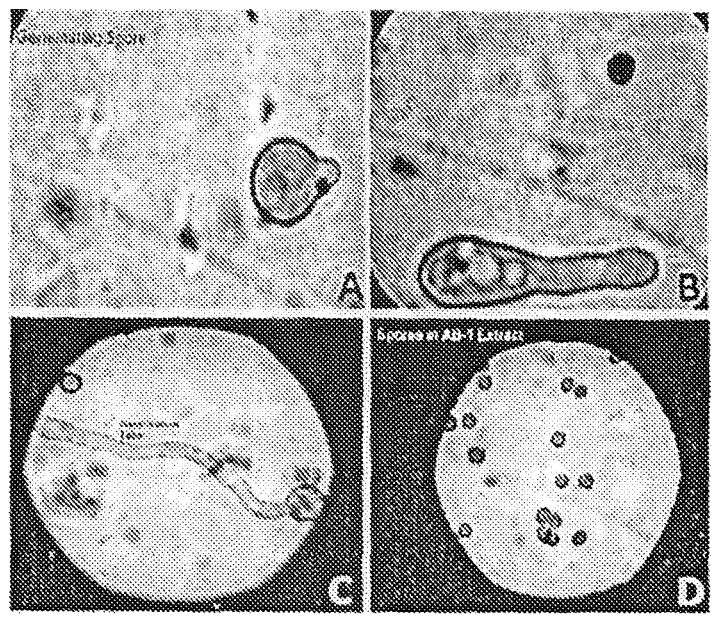

FIG. 14—Picture showing effect of antimicrobial and/or antifungal agent on spores of *Aspergillus niger*. (A, B & C) Spores of *Aspergillus niger* showing normal germination in PDB media; (D) Spores of *Aspergillus niger* failed to germinate in PDB media containing *Bacillus subtilis* ssp. *shriramensis* (MTCC-5674) extract.

Figure 15:
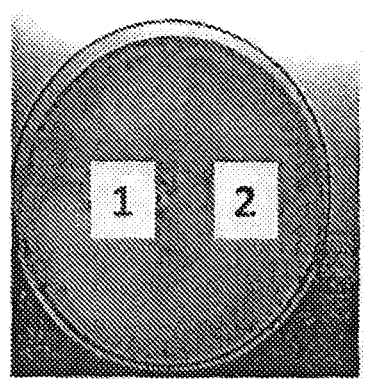

FIG. 15—Plate showing antimicrobial and/or antifungal activity of cell lysate against *Fusarium oxysporum*; (1) Well containing only lysozyme (to check the effect of lysozyme on fungus *Fusarium oxysporum*) and (2) Well containing cell lysate of *Bacillus subtilis* ssp. *shriramensis* (MTCC-5674).

Figure 16:
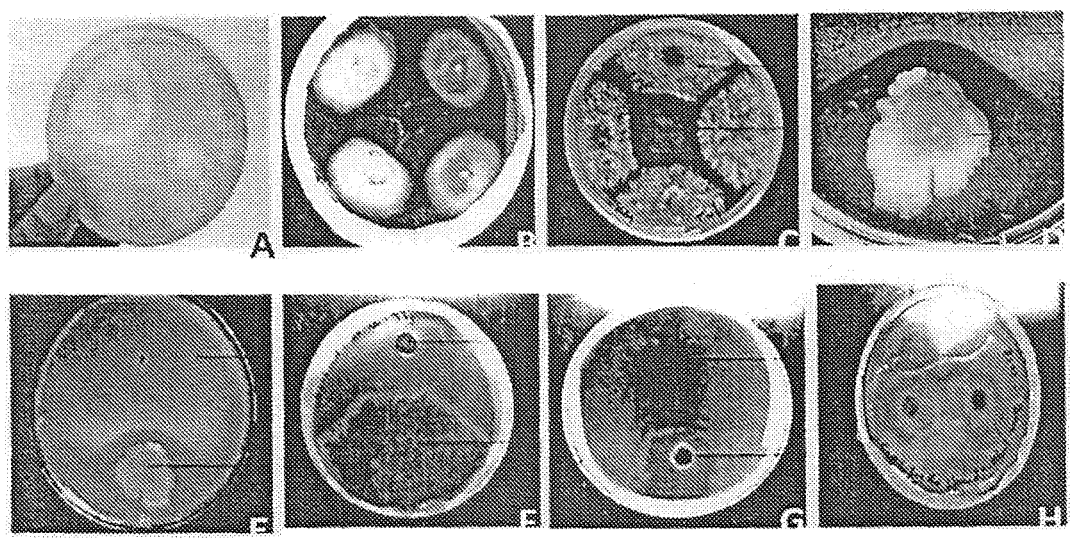

FIG. 16—Plate showing assay of antimicrobial and/or antifungal activity of *Bacillus subtilis* ssp. *shriramensis* (MTCC-5674) cells/extract against diverse types of plant pathogenic fungal and bacterial species. A. *Fusarium oxysporum*, B. *Sarocladium oryzae* C. *Trichoderma viridae D. *Colletotrichum capsicii* E. *Exerohilum turcicum* F. *Rhizoctonia solanii* G. *Macrophomina phaseolina* H. *Xanthomonas oryzae*

Figure 17:
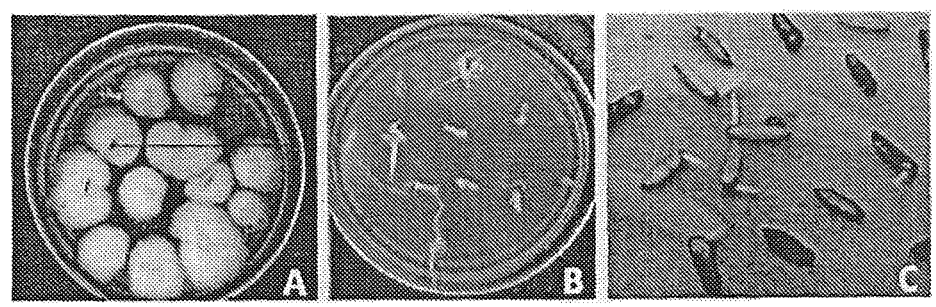

FIG. 17—Plate showing results of antimicrobial and/or antifungal activity of *Bacillus subtilis* ssp. *shriramensis* (MTCC-5674) extract on germination of rice seeds in presence of *Fusarium oxysporum*. (A) Rice seed treated with fungus *Fusarium oxysporum* spores; (B & C) Rice seeds treated with fungus *Fusarium oxysporum* and *Bacillus subtilis* ssp. *shriramensis* (MTCC-5674) extract.

Figure 18:
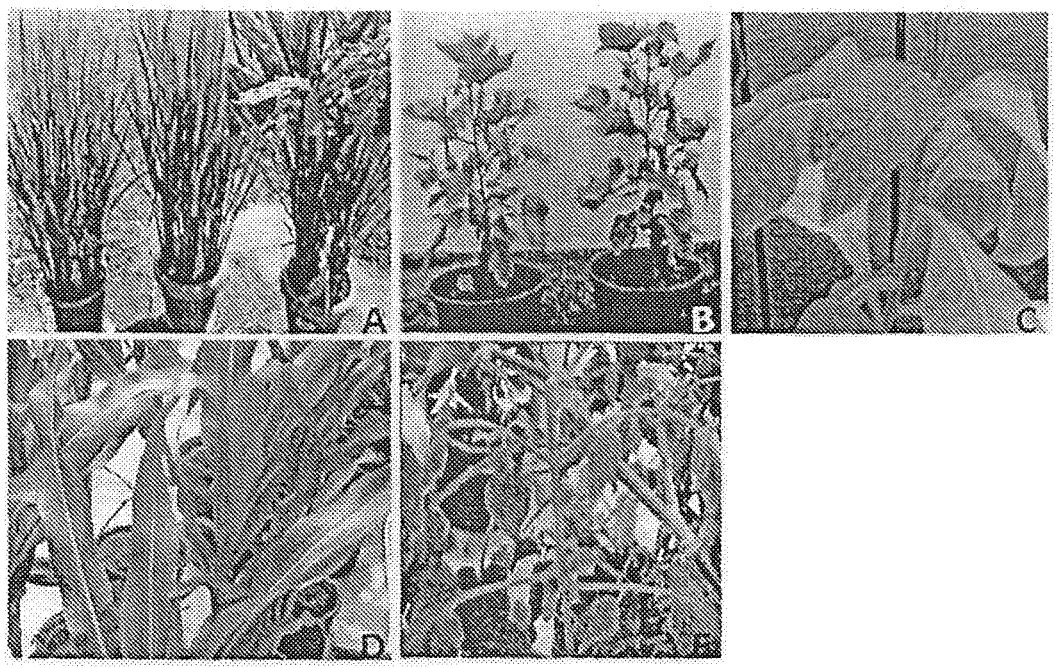

FIG. 18—Plate showing results of experiments to show absence of pathogenicity of *Bacillus subtilis* ssp. *shriramensis* (MTCC-5674) on various plant species. (A) Rice, (B) Cotton, (C) Tobacco, (D) Corn; and (E) Tomato.

Figure 19:
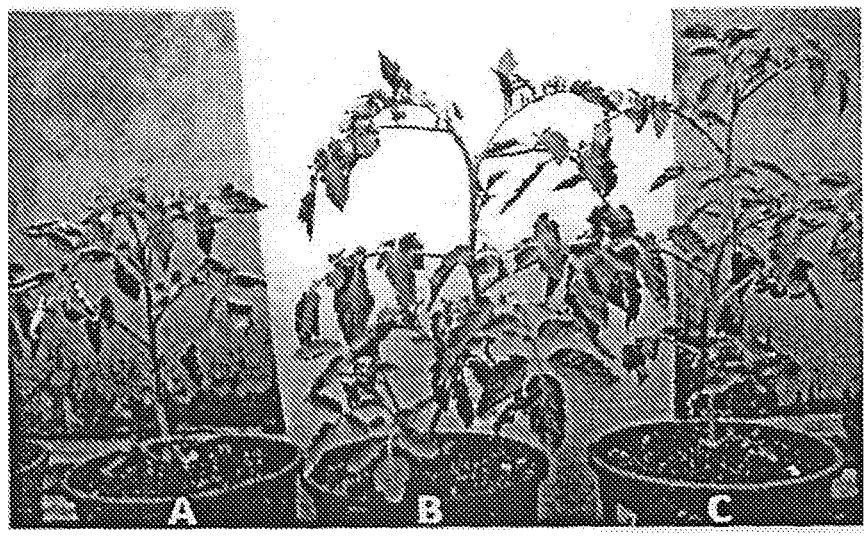

FIG. 19—Picture showing results of experiments to show action of *Bacillus subtilis* ssp. *shriramensis* (MTCC-5674) as bio-control agent. (A) Tomato plant infected with *Rhizoctonia solani* (NFCCI-3194) fungus. (B) Tomato plant with *Rhizoctonia solani* (NFCCI-3194) and *Bacillus subtilis* ssp. *shriramensis* (MTCC-5674) and (C) Control tomato plant (without *Rhizoctonia solani* fungus and *Bacillus subtilis* ssp. *shriramensis* (MTCC-5674).

Figure 20:
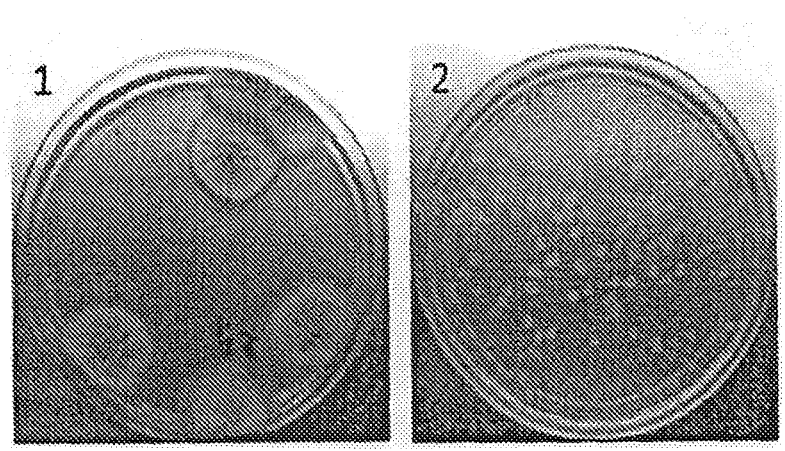

FIG. 20—Plates showing (1) *Penicillium oxalicum* (NFCCI-1997) fungal colonies and (2) *Bacillus subtilis* ssp. *shriramensis* (MTCC-5674) pure colonies.

Figure 21:
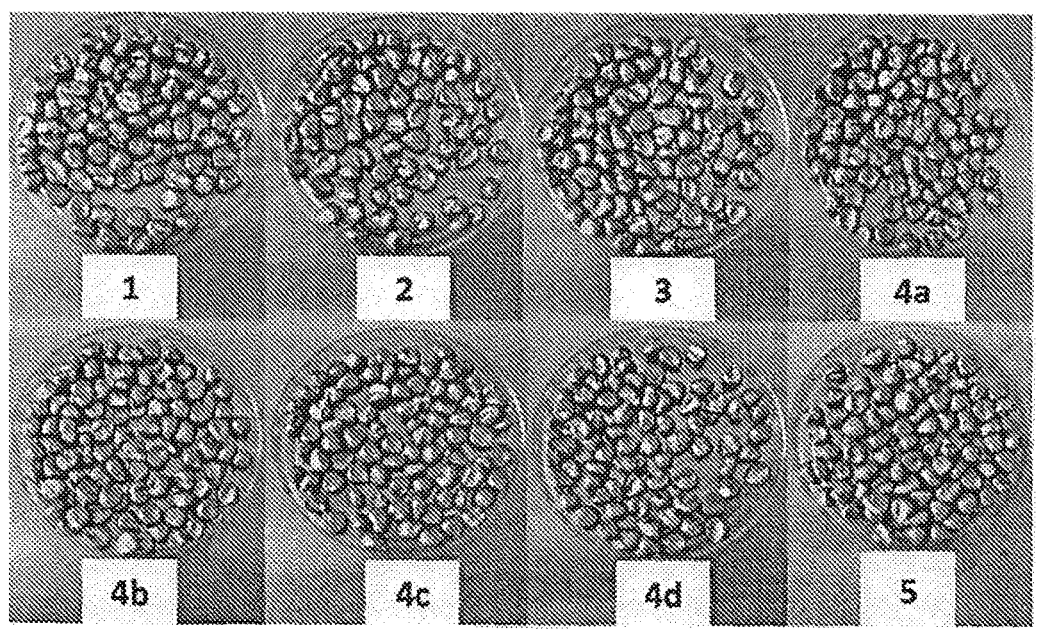

FIG. 21—Plate showing corn seeds coated with various formulations of antimicrobial/antifungal agent *Bacillus subtilis* ssp. *shriramensis* (MTCC-5674). 1. (Control-1) Seeds treated with the formulation which has no fungal pathogen and bio-control agent; 2. (Control-2) Seeds treated with the formulation which has no bio-control agent; 3. (Control-3) Seeds treated with the formulation which has commercial fungicide "Carbendazim WP50"; 4a. Seeds treated with the formulation which has *Bacillus subtilis* ssp. *shriramensis* cells ($5\times10^4$ cfu); 4b. Seeds treated with the formulation which has *Bacillus subtilis* ssp. *shriramensis* cells ($5\times10^5$ cfu); 4c. Seeds treated with the formulation which has *Bacillus subtilis* ssp. *shriramensis* cells ($5\times10^6$ cfu); 4d. Seeds treated with the formulation which has *Bacillus subtilis* ssp. *shriramensis* cells ($5\times10^7$ cfu) and 5. Seeds treated with the formulation which has only *Bacillus subtilis* ssp. *shriramensis* cells ($5\times10^7$ cfu).

Figure 22:
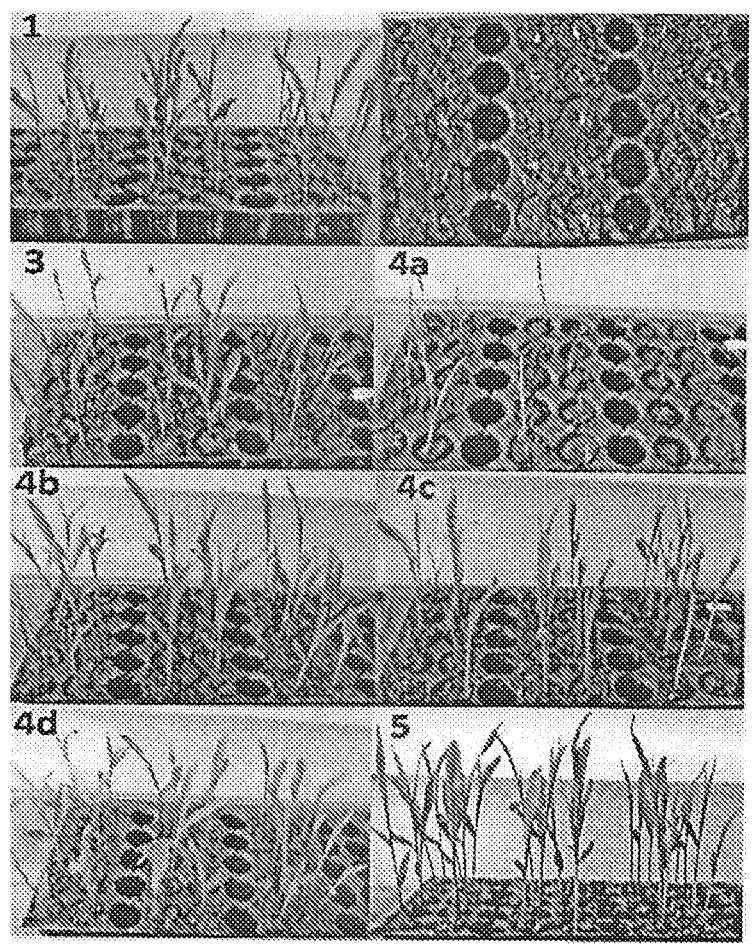

FIG. 22—Plate showing results of bio-control activity after 2 weeks of incubation. 1. (Control-1) Seeds treated with the formulation-1 which has no fungal pathogen and antifungal agent; 2. (Control-2) Seeds treated with the formulation-2 which has no bio-control agent; 3. (Control-3) Seeds treated with the formulation-3 which has commercial fungicide "Carbendazim WP50"; 4a. Seeds treated with the formulation-4a which has *Bacillus subtilis* ssp. *shriramensis* ($5\times10^4$ cfu); 4b. Seeds treated with the formulation-4b which has *Bacillus subtilis* ssp. *shriramensis* cells ($5\times10^5$ cfu); 4c. Seeds treated with the formulation-4c which has *Bacillus subtilis* ssp. *shriramensis* cells ($5\times10^6$ cfu); 4d. Seeds treated with the formulation-4d which has *Bacillus subtilis* ssp. *shriramensis* cells ($5\times10^7$ cfu) and 5. Seeds treated with the formulation-5 which has only *Bacillus subtilis* ssp. *shriramensis* cells ($5\times10^7$ cfu).

Figure 23:
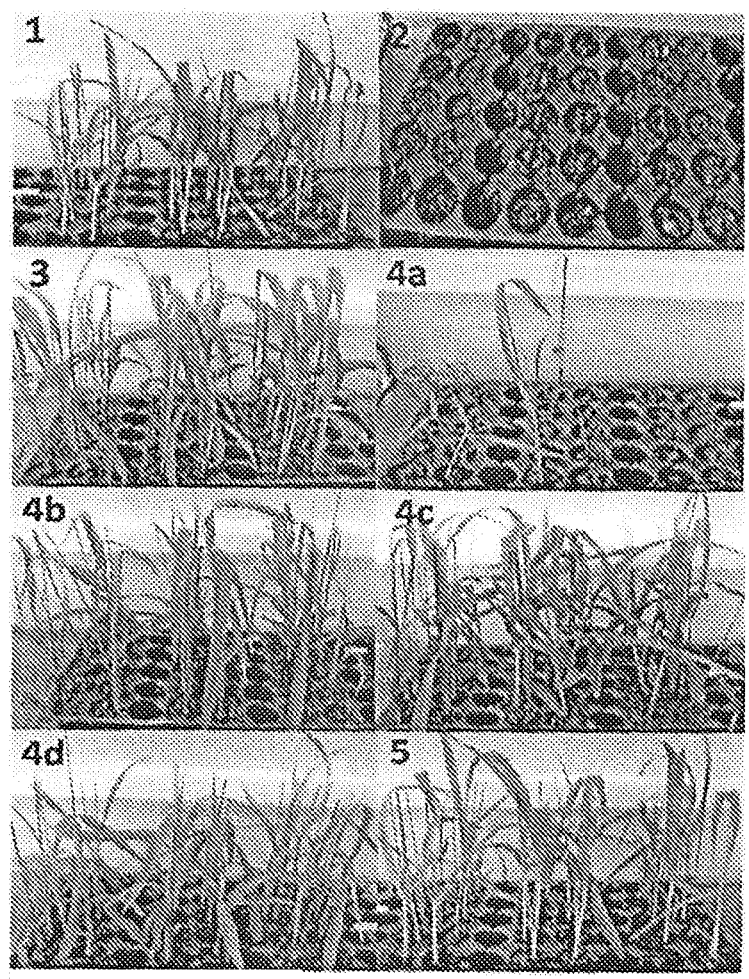

FIG. 23—Plate showing results of bio-control activity after 4 weeks of incubation. 1. (Control-1) Seeds treated with the formulation-1 which has no fungal pathogen and antifungal agent; 2. (Control-2) Seeds treated with the formulation-2 which has no bio-control agent; 3. (Control-3) Seeds treated with the formulation-3 which has commercial fungicide "Carbendazim WP50"; 4a. Seeds treated with the formulation-4a which has *Bacillus subtilis* ssp. *shriramensis* ($5\times10^4$ cfu); 4b. Seeds treated with the formulation-4b which has *Bacillus subtilis* ssp. *shriramensis* cells ($5\times10^5$ cfu); 4c. Seeds treated with the formulation-4c which has *Bacillus subtilis* ssp. *shriramensis* cells ($5\times10^6$ cfu); 4d. Seeds treated with the formulation-4d which has *Bacillus subtilis* ssp. *shriramensis* cells ($5\times10^7$ cfu) and 5. Seeds treated with the formulation-5 which has only *Bacillus subtilis* ssp. *shriramensis* cells ($5\times10^7$ cfu).

Figure 24:
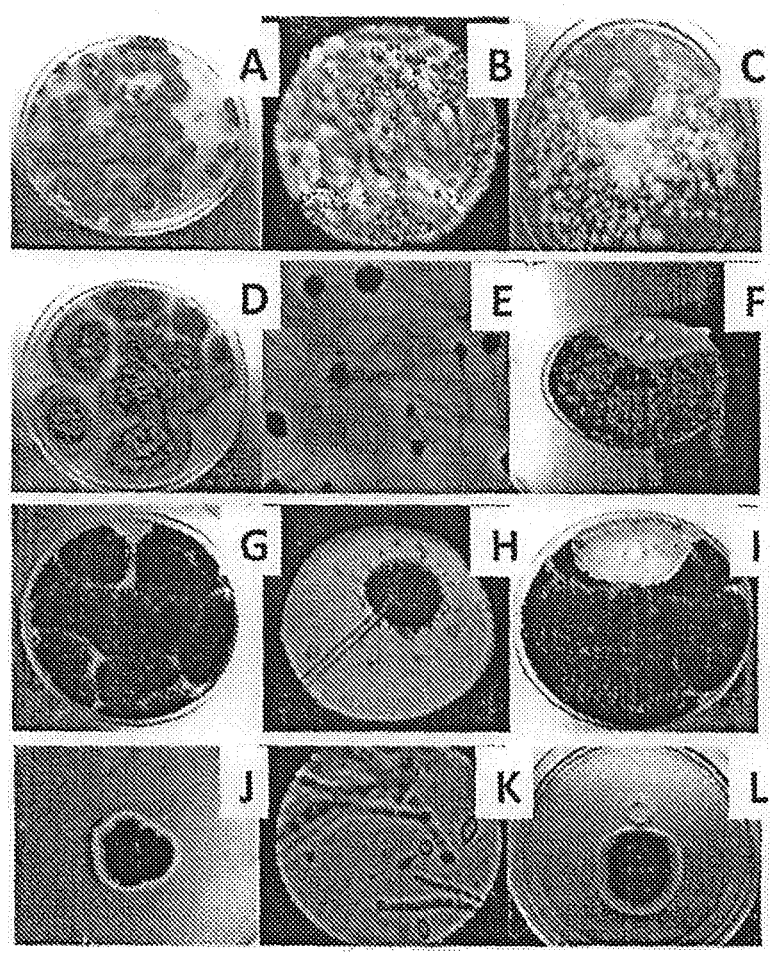

FIG. 24—Assay of antifungal and/or antimicrobial activity against a variety of human pathogenic fungal species. A, B and C—Assay of antifungal and/or antimicrobial activity against *Penicillium* spp. (A) *Penicillium* spp. fungal colonies (B) Mycelium and (C) Effect of *Bacillus subtilis* ssp. *shriramensis* (MTCC-5674) culture filtrate. D, E and F—Assay of antifungal and/or antimicrobial activity against *Aspergillus flavus* (D) Fungal colonies (E) Mycelium and (F) Effect of *Bacillus subtilis* ssp. *shriramensis* (MTCC-5674) culture filtrate. G, H and I—Assay of antifungal and/or antimicrobial activity against *Aspergillus niger*. (G) Fungal colonies (H) Mycelium and (I) Effect of *Bacillus subtilis* ssp. *shriramensis* (MTCC-5674) culture filtrate. J, K and L—Assay of antifungal and/or antimicrobial activity against unknown fungus causing skin infection. (J) Fungal colonies (K) Conidia and (L) Effect of *Bacillus subtilis* ssp. *shriramensis* (MTCC-5674) culture filtrate.

Figure 25:
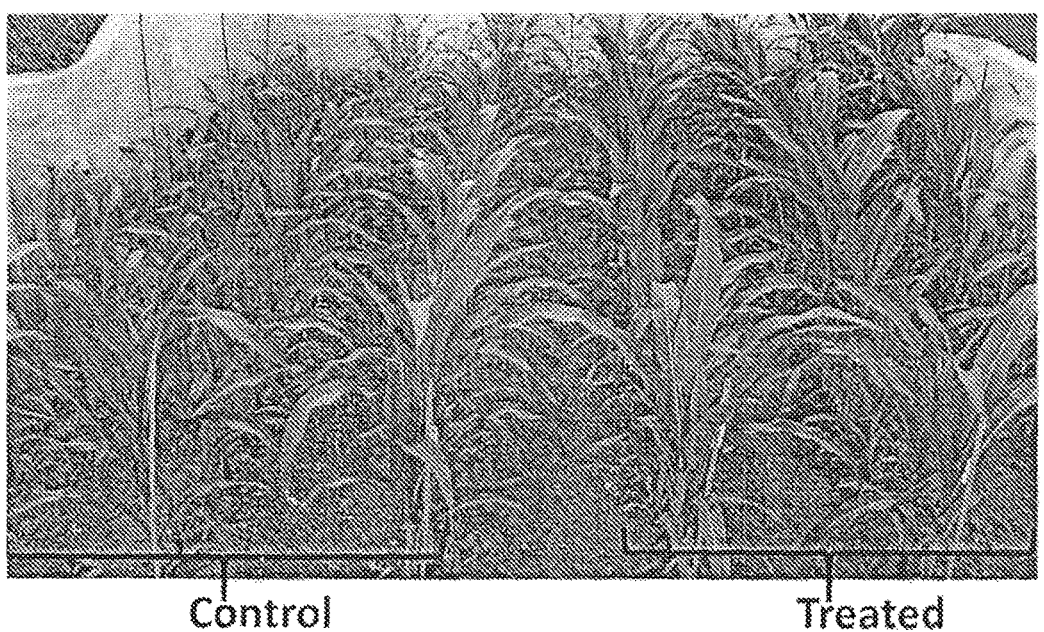

FIG. 25—Effect of *Bacillus subtilis* ssp. *shriramensis* (MTCC-5674) formulation on growth and development of Corn. The corn seed treated with formulation containing *Bacillus subtilis* ssp. *shriramensis* (MTCC-5674) showed higher growth rate, biomass and grain yield.

ISOLATION AND IDENTIFICATION OF THE NOVEL BACTERIUM

The inventors collected air samples from 18 different locations in Hyderabad and Patancheru (Telangana, India) while conducting a study on air flora. Disposable petri plates containing media (T3 Medium, Travers, et al., 1987) were prepared in the laboratory and exposed to air at different locations. The exposed plates were sealed and incubated at 30° C. in lab incubator. In one of the plates exposed to air in Patancheru area, a bacterial colony surrounded by fungal mycelium was observed (FIG. 1A). Despite continued incubation, the clearance zone was maintained and growth of fungal mycelium remained restricted to the periphery of clearance zone. The microorganisms from this colony were subjected to purification by using standard methods of microbiology (FIG. 1B). The individual colonies were tested against a common fungus *Fusarium oxysporum* (FIG. 2).

One of the colonies showed inhibition of fungal growth and a clearance zone was observed (FIG. 2). Microscopical examination of the bacteria from the colony revealed a rod shaped motile bacterium (FIG. 5). After six days of incubation in the culture medium the bacteria produced spores. The colonies of the bacteria were mucoid, raised, circular, smooth, and creamy to off-white in color (FIG. 4), and cells showed variable gram staining (FIG. 5).

A range of biochemical tests including carbohydrate fermentation, catalase activity, oxidation-fermentation test, starch hydrolysis, hydrogen sulphide production test, oxidase activity test, desoxycholate agar test were carried out. The results of these tests confirmed that the bacteria is catalase positive, possess amylase activity, strongly aerobic, does not produce hydrogen sulfide, oxidase positive and gram variable.

For identification of bacteria 16S DNA sequencing and FAME analysis was carried out. The results of both studies showed that the bacteria is showing 0.37% difference in 16S DNA sequence and FAME similarity index of 0.827; with *Bacillus subtilis* ssp. *subtilis* and 0.84% difference in 16S DNA sequence and FAME similarity index of 0.749 with *Bacillus atrophaeus*. Thus, the results suggest that this bacterium is related to *Bacillus subtilis* and *Bacillus atrophaeus*, but not identical to any of the catalogued bacterial species in ATCC collection.

Results of 16S DNA Sequence Comparison

| Match | % Difference | Length | Library Entry Name |
| --- | --- | --- | --- |
| 1 | 0.19 | 535 | *Bacillus subtilis* ssp. *subtilis* |
| 2 | 0.84 | 535 | *Bacillus atrophaeus* |
| 3 | 1.03 | 535 | *Bacillus amyloliquifaciens* |

Results of FAME analysis comparison

| S. No. | Similarity Index | Library Entry Name |
| --- | --- | --- |
| 1 | 0.827 | *Bacillus subtilis* |
| 2 | 0.749 | *Bacillus atrophaeus* |

The isolated bacterium is a new member of sub-species of the genus *Bacillus*. According to bacterial nomenclature convention, the novel bacterial species was named as *Bacillus subtilis* ssp. *shriramensis*. The bacterium was deposited in the Microbial Type Culture Collection (MTCC) at the Instiutue of Microbial Technology (IMTECH), Sector 39-A, Chandigarh- 160036, India, On Dec. 14, 2011. The deposition number of this novel species is (MTCC-5674).

Characteristic Features of the Novel Microbe Having Accession/Deposition Number (MTCC-5674) Provided by the Present Invention The bacterium is a rod shaped measuring 2.45×0.88 μm, motile, spore forming, gram variable; colonies are smooth, mucoid, off-white to creamish in early stages but turn wrinkled on prolonged incubation. The bacterium transforms into spore as the nutrients in the medium deplete, normally the process of sporulation takes place in 4 days of incubation in 10 ml medium containing 100 μl of $5 \times 10^8$ cells inoculum in a 25×150 mm culture tube at 30° C. and shaking at 200 rpm.

The novel bacterium, *Bacillus subtilis* ssp. *shriramensis* having accession number (MTCC-5674) exhibits antimicrobial and/or antifungal activity. The extract of the novel bacterium, *Bacillus subtilis* ssp. *shriramensis* having accession number (MTCC-5674) exhibits antimicrobial and/or antifungal activity. The range of potential applications and uses of the bacterium are extensive.

The present invention provides a method of producing the antimicrobial and/or antifungal extract from the novel bacterium, *Bacillus subtilis* ssp. *shriramensis* having accession number (MTCC-5674).

Production and Isolation of Antimicrobial and/or Antifungal Agent

Composition of culture medium for the growth of *Bacillus subtilis* ssp. *shriramensis* having accession number (MTCC-5674) is as follows 1. Tryptone: 0.32% (w/v)
2. Tryptose: 0.24% (w/v)
3. Yeast Extract: 0.18% (w/v)
4. $NaH_2PO_4.H_2O$: 0.044 M
5. $Na_2HPO_4$: 0.062 M
6. $MnCl_2$: 0.000 5% (w/v)
   pH=6.8

1. The medium was prepared as per the method given in Annexure-I (1) and 100 ml aliquots were transferred into 500 ml conical flasks. The media was sterilised by autoclaving at 121° C. for 15 min.
2. Each flask was inoculated with a single pure colony of *Bacillus subtilis* ssp. *shriramensis* (MTCC-5674) and incubated at 30° C., 200 rpm for 60 hours.

Isolation of Antimicrobial and/or Antifungal Agent from Culture Medium

Following the growth of bacteria in T3 broth for 60 hours, the culture was centrifuged at 12000 rpm for 10 min at 4° C. The supernatant was collected and filtered using 0.22 μm disc filter (Millipore/Sartorius). The filtrate was preserved under appropriate storage conditions for detailed experiments to study antimicrobial and/or antifungal activity.

The present invention particularly provides a novel microorganism, *Bacillus subtilis* ssp. *shriramensis* having accession number (MTCC-5674) and a method for the production of antimicrobial and/or antifungal composition from the novel bacterium and/or its extract or a mixture of the novel bacterium and/or its extract.

One embodiment of the present invention provides an isolated novel bacterium, belonging to *Bacillus subtilis* ssp. *shriramensis* exhibiting antimicrobial and/or antifungal activity, having accession number (MTCC-5674).

In one embodiment of the present invention is provided the novel bacterium designated as *Bacillus subtilis* ssp. *shriramensis* having accession number (MTCC-5674).

In another embodiment of the present invention there is provided a pure culture of the novel bacterium, *Bacillus subtilis* ssp. *shriramensis* having accession number (MTCC-5674).

In one embodiment of the present invention there is provided an extract of the novel bacterium, *Bacillus subtilis* ssp. *shriramensis* having accession number (MTCC-5674) wherein the extract exhibits antimicrobial and/or antifungal activity.

In another embodiment of the present invention there is provided an extract of the novel bacterium, *Bacillus subtilis* ssp. *shriramensis* having accession number (MTCC-5674) wherein the extract exhibiting antimicrobial and/or antifungal activity is an aqueous extract. In yet another embodiment of the present invention there is provided a process for the production of the extract of the novel bacterium, *Bacillus subtilis* ssp. *shriramensis* having accession number (MTCC-5674) where in the process comprises growing the novel bacterium, *Bacillus subtilis* ssp. *shriramensis* having accession number (MTCC-5674) in a nutrient medium and recovering the extract having antifungal activity by using conventional methods.

In another embodiment of the present invention there is provided a process for the production of the extract of the novel bacterium, *Bacillus subtilis* ssp. *shriramensis* having accession number (MTCC-5674) wherein the process comprises growing the novel bacterium, *Bacillus subtilis* ssp. *shriramensis* having accession number (MTCC-5674) under aerobic conditions.

In yet another embodiment of the present invention there is provided a process for the production of the extract of the novel bacterium, *Bacillus subtilis* sp. *shriramensis* having accession number (MTCC-5674) wherein the process comprises growing the novel bacterium, *Bacillus subtilis* ssp. *shriramensis* in a nutrient medium, recovering the extract having antimicrobial and/or antifungal activity and optionally comprises concentrating the extract using conventional methods.

In one embodiment of the present invention, there is provided a composition comprising the novel bacterium, *Bacillus subtilis* ssp. *shriramensis* having accession number (MTCC-5674) wherein the composition has antimicrobial and/or antifungal activity.

In another embodiment of the present invention, there is provided a composition comprising the extract of the novel bacterium, *Bacillus subtilis* ssp. *shriramensis* having accession number (MTCC-5674) wherein the composition has antimicrobial and/or antifungal activity.

In another embodiment of the present invention, there is provided a composition comprising the novel bacterium, *Bacillus subtilis* ssp. *shriramensis* having accession number (MTCC-5674) and the extract of the novel bacterium, *Bacillus subtilis* ssp. *shriramensis* having accession number (MTCC-5674) wherein the composition has antimicrobial and/or antifungal activity.

In one embodiment of the present invention, there is provided a composition comprising the novel bacterium, *Bacillus subtilis* ssp. *shriramensis* having accession number (MTCC-5674) and/or an extract of the said novel bacterium, *Bacillus subtilis* ssp. *shriramensis*, or a combination thereof that optionally comprises one or more antimicrobial and/or antifungal agents.

In another embodiment of the present invention, there is provided a composition comprising an extract of the novel bacterium, *Bacillus subtilis* ssp. *shriramensis* having accession number (MTCC-5674) that optionally comprises one or more antimicrobial and/or antifungal agents.

In yet another embodiment of the present invention there is provided a composition comprising the combination of the novel bacterium, *Bacillus subtilis* ssp. *shriramensis* having accession number (MTCC-5674) and its extract that optionally comprises one or more antimicrobial and/or antifungal agents.

In one embodiment of the present invention there is provided a composition comprising the novel bacterium, *Bacillus subtilis* ssp. *shriramensis* having accession number (MTCC-5674) or an extract of the novel bacterium, *Bacillus subtilis* ssp. *shriramensis* having accession number (MTCC-5674) or a combination thereof that optionally comprises agriculturally or pharmaceutically acceptable carrier.

In another embodiment of the present invention there is provided a composition comprising the novel bacterium, *Bacillus subtilis* ssp. *shriramensis* having accession number (MTCC-5674) that optionally comprises agriculturally or pharmaceutically acceptable carrier.

In yet another embodiment of the present invention there is provided a composition containing an extract of the novel bacterium, *Bacillus subtilis* ssp. *shriramensis* having accession number (MTCC-5674) that optionally comprises agriculturally or pharmaceutically acceptable carrier.

In still another embodiment of the present invention there is provided a composition comprising the combination of the novel bacterium, *Bacillus subtilis* ssp. *shriramensis* having accession number (MTCC-5674) and an extract of the said novel bacterium, *Bacillus subtilis* ssp. *shriramensis*, which optionally comprises agriculturally acceptable carrier (Sec Annexure III).

In one embodiment of the present invention there is provided a method for inhibiting growth of pathogenic fungi and/or bacteria, wherein said method comprises contacting the pathogenic fungi and/or bacteria with an effective amount of the novel bacterium, *Bacillus subtilis* ssp. *shriramensis* having accession number (MTCC-5674) or a composition comprising the said novel bacterium, or its extract or a combination thereof.

In one embodiment of the present invention there is provided a method for inhibiting growth of pathogenic fungi and/or bacteria, wherein said method comprises contacting the pathogenic fungi and/or bacteria with an effective amount of the novel bacterium, *Bacillus subtilis* ssp. *shriramensis* having accession number (MTCC-5674).

In another embodiment of the present invention there is provided a method for inhibiting growth of pathogenic fungi and/or bacteria, wherein said method comprises contacting the pathogenic fungi and/or bacteria with an effective amount of a composition comprising the novel bacterium, *Bacillus subtilis* ssp. *shriramensis* having accession number (MTCC-5674).

In yet another embodiment of the present invention there is provided a method for inhibiting growth of pathogenic fungi and/or bacteria, wherein said method comprises contacting the pathogenic fungi and/or bacteria with an effective amount of a composition comprising an extract of the novel bacterium, *Bacillus subtilis* ssp. *shriramensis* (MTCC-5674) wherein the extract has antimicrobial and/or antifungal activity.

In yet another embodiment of the present invention there is provided a method for inhibiting growth of pathogenic fungi and/or bacteria, wherein said method comprises contacting the pathogenic fungi and/or bacteria with an effective amount of a composition comprising the novel bacterium, *Bacillus subtilis* ssp. *shriramensis* (MTCC-5674) and an extract of the said novel bacterium, *Bacillus subtilis* ssp. *shriramensis*, wherein the extract has antimicrobial and/or antifungal activity.

In one embodiment of the present invention there is provided a use of the novel bacterium, *Bacillus subtilis* ssp. *shriramensis* having accession number (MTCC-5674) or a composition comprising the said novel bacterium or its extract or a combination thereof, for the preparation of an antimicrobial and/or antifungal composition for inhibiting the growth of pathogenic fungi and/or bacteria.

In another embodiment of the present invention there is provided a use of the novel bacterium, *Bacillus subtilis* ssp. *shriramensis* having accession number (MTCC-5674) for the preparation of an antimicrobial and/or antifungal composition for inhibiting the growth of pathogenic fungi and/or bacteria.

In another embodiment of the present invention there is provided a use of the composition comprising the novel bacterium, *Bacillus subtilis* ssp. *shriramensis* (MTCC-5674) for the preparation of an antimicrobial and/or antifungal composition for inhibiting the growth of pathogenic fungi and/or bacteria.

In another embodiment of the present invention there is provided a use of the composition comprising an extract of the novel bacterium, *Bacillus subtilis* ssp. *shriramensis* (MTCC-5674) for the preparation of an antimicrobial and/or antifungal composition for inhibiting the growth of pathogenic fungi and/or bacteria.

In another embodiment of the present invention there is provided a use of the composition comprising the extract of the novel bacterium, *Bacillus subtilis* ssp, *shriramensis* (MTCC-5674) and an extract of the said novel bacterium, *Bacillus subtilis* ssp. *shriramensis*, for the preparation of an antimicrobial and/or antifungal composition for inhibiting the growth of pathogenic fungi and/or bacteria.

In another embodiment, there is provided a pharmaceutical and agriculturally effective composition comprising the novel bacterium, *Bacillus subtilis* ssp. *shriramensis* having accession number (MTCC-5674).

In another embodiment, there is provided a pharmaceutical and agriculturally effective composition comprising the extract of the novel bacterium, *Bacillus subtilis* ssp. *shriramensis* (MTCC-5674).

In yet another embodiment of the present invention there is provided a method of producing the said effective composition from the novel bacterium, *Bacillus subtilis* ssp. *shriramensis* having accession number (MTCC-5674).

In yet another embodiment of the present invention, the steps and time required for the production of the said composition/extract are kept at the minimum duration coupled with the maximum recovery of the compound.

Other Advantages or Benefits of the Present Invention

The bacterium *Bacillus subtilis* ssp. *shriramensis* (MTCC-5674) along with antimicrobial and/or antifungal agent also produces strong thermophilic protease and amylase which are active even after exposure to high temperature i.e., 121° C. for 15 min.

The present invention is further explained by the following examples. However, the present invention is not limited to these examples in any manner. The following examples is intended to illustrate the working of disclosure and not intended to take restrictively to apply any limitations on the scope of the present invention. Those persons skilled in the art will understand that the equivalent substitutes to the specific substances described herein, or the corresponding improvements are considered to be within the scope of the invention.

DETAILED METHODOLOGY IS EXPLAINED IN THE FOLLOWING EXAMPLES

The methods employed in the present work are well-known in microbiology with the respective parameters varied and optimized for the present study.

Example 1

1.1 Collection and Preliminary Screening of Air Samples

Air sampling was carried out at different locations in Hyderabad and Patancheru (Telangana, India). Disposable Petri plates containing T3 medium were prepared in the laboratory and exposed to air at different locations. The exposed plates were sealed and incubated at 30° C. in lab incubator. In one of the plates exposed to air in Patancheru area, a bacterial colony surrounded by fungal mycelium was observed.

1.2 Preliminary Screening of Air Samples for Antimicrobial and/or Antifungal Activity Despite continued incubation the clearance zone was maintained and growth of fungal mycelium remained restricted to the periphery of clearance zone. The microorganisms from this colony were subjected to purification by using standard methods of microbiology (FIG. 1B). The individual colonies were tested against a common fungus *Fusarium oxysporum* (FIG. 2). One of the colonies showed inhibition of fungal growth and a clearance zone was observed (FIG. 2).

1.3 Screening of Novel Isolate

Evaluation of the bacteria under microscope revealed that it is a rod shaped motile bacterium (FIG. 5). After six days of incubation the bacteria produced spores.

The colonies of the bacteria were mucoid, raised, circular, smooth, and creamish to off-white in color (FIG. 4) and the cells showed variable gram staining.

Example 2

2.1 Characterization and Identification of the Novel Microorganism 2.1.1 Characterization of the Novel Isolate *Bacillus subtilis* ssp. *shriramensis* Having Accession Number (MTCC-5674)

A range of biochemical tests, including carbohydrate fermentation, catalase test, oxidation-fermentation test, starch hydrolysis, hydrogen sulfide production test, oxidase activity test, were carried out. The results of these tests confirmed that the bacterium is catalase positive, amylase positive, oxydase positive and strongly aerobic.

2.1.1.1 *Bacillus subtilis* ssp. *shriramensis* (MTCC-5674)—Colony Morphology

Colonies of *Bacillus subtilis* ssp. *shriramensis* (MTCC-5674) are mucoid, raised, circular, smooth, and creamish to off-white in color (FIG. 4).

2.1.1.2 Culture Characteristics

*Bacillus subtilis* ssp. *shriramensis* (MTCC-5674) shows optimum growth at 30° C. (can grow from 15° C. to 55° C.). As it is an aerobic bacterium, it requires adequate oxygen for its growth, needs continuous shaking for culturing in broth.

2.1.1.3 Cell Morphology

*Bacillus subtilis* ssp. *shriramensis* (MTCC-5674) cells are rod shaped, diplobacilli and motile (FIG. 5).

2.1.1.3.1 Comparison of Colony Growth and Morphology of *Bacillus subtilis* ssp. *shriramensis* (MTCC-5674) with that of *Bacillus subtilis* and *Bacillus atrophaeus*

|  | *B. subtilis* ssp. *shriramensis* | *B. subtilis* ssp, *subtilis* | *B. atraphaeus* |
|---|---|---|---|
| Colony Morphology | Mucoid, circular, smooth, (rough after prolonged incubation), 2.0-4.0 mm in diameter. | Mucoid, circular, entire, opaque, 2.0-4.0 mm in diameter | Opaque, smooth, circular, entire and 1.0-2.0 mm diameter (Nakamura L. K. 1989). |
| Colony Color | Cream to off-white | Off-white to brown | Dark brown to black |

2.1.1.4 Catalase Test

Material

Culture tubes of *Bacillus subtilis* ssp. *shriramensis* (MTCC-5674)

Hydrogen Peroxide

Method

Three tubes containing LB medium were labelled as "test", "positive control" and "negative control" a loop full of *Bacillus subtilis* ssp. *shriramensis* (MTCC-5674), *Escherichia coli* and *Streptococcus pneumonia* were inoculated in the tubes respectively. Following incubation at 30° C. for 24 hours, few drops of hydrogen peroxide were added in all the tubes and observed for formation of bubbles.

Result

Gas bubbles were formed both in "test" and "positive control" tubes indicating that the *Bacillus subtilis* ssp. *shriramensis* (MTCC-5674) is catalase positive (FIG. 6).

2.1.1.5 Starch Hydrolysis

Material

*Bacillus subtilis* ssp. *shriramensis* (MTCC-5674) culture filtrate

Starch agar plates
Iodine
Incubator
Method

The starch agar medium was prepared as per the method provided in the Annexure-I (VI). Two wells were made at equal distances in the plate containing starch agar medium and labelled as "test" and "negative control". An aliquot of 500 µl each of *Bacillus subtilis* ssp. *shriramensis* (MTCC-5674) culture filtrate and sterile distilled water were dispensed into the wells labelled "test" and "negative control". The plate was incubated at 50° C. for 4 hours.

Result

After 4 hours of incubation, the blue color surrounding the test well disappeared indicating that the *Bacillus subtilis* ssp. *shriramensis* (MTCC-5674) culture filtrate has amylolytic activity. No change in the blue color was observed in the area surrounding control well (FIG. 7).

2.1.1.6 O/F (Oxidation-Fermentation) Test

Material
Hugsh Leifson's OF Basal Medium
Test tubes
*E. coli* culture
*Bacillus subtilis* ssp. *shriramensis* (MTCC-5674)
Incubator
Method Three tubes containing Hugsh Leifson's OF basal medium (OFBM) (Annexure-I (VII)) were labelled as "negative control", "positive control" and "test" and a loop full of *Alcaligenes faecalis, Escherichia coli* and *Bacillus subtilis* ssp. *shriramensis* (MTCC-5674) was inoculated in the tubes respectively. The tubes were incubated at 30° C. for 48 hours and observed for change of color.

Results

It has been concluded from the observations that the test organism (*Bacillus subtilis* ssp. *shriramensis* (MTCC-5674) is strictly aerobic as it did not ferment carbohydrate (neither gas formation nor the color change) deep inside the medium. Due to availability of oxygen on the surface of medium some color change was observed. Whereas *E. coli* grew very well deep inside the medium and fermented the carbohydrates (both gas formation and change in color of the medium) indicating that it is a facultative anaerobe (FIG. 8). In the negative control neither gas formation nor color change was observed.

2.1.1.7 Hydrogen Sulfide Production Test

Material
SIM (Sulfide Indole Motility) medium
Culture tubes
*E. coli* culture
*Bacillus subtilis* ssp. *shriramensis* (MTCC-5674)
Incubator
Method The tubes containing SIM [Sulfide Indole Motility, {Annexure-I (VII)}] medium were labelled as "negative control" and "test" and a loop full of *E. coli* and *Bacillus subtilis* ssp. *shriramensis* (MTCC-5674), were inoculated in the tubes respectively, and incubated at 30° C. for 24 hours and observed for color change.

Result

From the observations, it has been concluded that the test organism is negative for $H_2S$ production as the medium did not turn black. The same result was observed in the negative control (FIG. 9).

2.1.1.8 Effect of pH on the Growth of *Bacillus subtilis* ssp. *shriramensis* (MTCC-1674)

Culture tubes containing standard culture medium (LB) adjusted to different pH values ranging from 3.4 to 11.0 (acidic to basic) were used to grow *Bacillus subtilis* ssp. *shriramensis* (MTCC-5674) under standard conditions. Growth of *Bacillus subtilis* ssp. *shriramensis* (MTCC-5674) was observed in a pH range of 6.4 to 7.2 and the optimum pH was found to be 7.0.

2.1.1.9 Antibiotic Sensitivity Test of *Bacillus subtilis* ssp. *shriramensis* (MTCC-5674)

A 24 hours old *Bacillus subtilis* ssp. *shriramensis* (MTCC-5674) culture was spread over the surface of T3 agar. Different antibiotic discs were placed on the surface of the T3 agar plates labelled with the respective antibiotic. The plates were incubated at 30° C. for 24 hours.

TABLE 1

Observations on antibiotic sensitivity of *Bacillius subtilis* ssp. *shriramensis* (MTCC-5674) RES - Resistant, INT - Intermediate, SEN - Sensitive

| S. No. | Antibiotic | Code | Zone | Result | Standards RES | INT | SEN |
|---|---|---|---|---|---|---|---|
| 1 | Ampicillin | A10 | 0 | RES | 13 | 14-16 | 17 |
| 2 | Gentamicin | G10 | 20 | SEN | 12 | 13-14 | 15 |
| 3 | Tobramycin | TB10 | 15 | SEN | 12 | 13-14 | 15 |
| 4 | Carbenicillin | CB100 | 15 | RES | 19 | 20-22 | 23 |
| 5 | Vancomycin | VA30 | 20 | SEN | <15 | | 15 |
| 6 | Oxacillin | OX1 | 11 | INT | 10 | 11-12 | 13 |
| 7 | Novobiocin | NY30 | 24 | SEN | 17 | 18-21 | 22 |
| 8 | Sulfisoxazole | SF300 | 33 | SEN | 12 | 13-16 | 17 |
| 9 | Amikacin | AK30 | 15 | INT | 14 | 15-16 | 17 |
| 10 | Kanamycin | K10 | 13 | RES | 13 | 14-17 | 18 |
| 11 | Streptomycin | S10 | 12 | INT | 11 | 12-14 | 15 |
| 12 | Cephalothin | CH30 | 40 | SEN | 14 | 15-17 | 18 |
| 13 | Chloramphenicol | C30 | 25 | SEN | 12 | 13-17 | 18 |
| 14 | Erythromycin | E15 | 16 | INT | 13 | 14-22 | 23 |
| 15 | Enrofloxacin | EX10 | 41 | RES | N/A | N/A | N/A |
| 16 | Lincomycin | L10 | 12 | RES | N/A | N/A | N/A |
| 17 | Amoxicillin | AC30 | 0 | RES | 19 | | 20 |
| 18 | Clindamycin | CD2 | 10 | RES | 14 | 15-20 | 21 |
| 19 | Ceftriaxone | C130 | 28 | SEN | 13 | 14-20 | 21 |
| 20 | Bacitracin | B10 | 21 | SEN | 8 | 9-12 | 13 |
| 21 | Neomycin | N30 | 12 | RES | 12 | 13-16 | 17 |
| 22 | Azithromycin | AT15 | 10 | RES | 13 | 14-17 | 18 |

Result

It has been concluded from the observations that *Bacillus subtilis* ssp. *shriramensis* (MTCC-5674) is resistant to the antibiotics—ampicillin, carbenicillin, kanamycin, enrofloxacin, lincomycin, amoxicillin, clindamycin, neomycin, azithromycin. The test bacterium is sensitive to gentamicin, tobramicin, vancomicin, novobiocin, sulfisoxazole, cephalothin, chloramphenicol, ceftriaxone and bacitracin and showed intermediate resistance to oxacillin, amikacin, streptomycin and erythromycin.

2.1.2 Identification of the Novel Isolate *Bacillus subtilis* ssp. *shriramensis* (MTCC-5674)

For identification of bacteria, 16S DNA sequencing and FAME analysis were carried out. The results of both studies showed that the bacteria is showing 0.37% difference in 16S DNA sequence and FAME similarity index of 0.827; with *Bacillus subtilis* ssp. *subtilis* and 0.84% difference in 16S DNA sequence and FAME similarity index of 0.749 with *Bacillus atrophaeus*. Thus, the results indicate that this bacterium is related to *Bacillus subtilis* and *Bacillus atrophaeus*, but not identical to any of the catalogued bacterial species in ATCC collection.

2.1.2.1 Results of 16S DNA Sequence Comparison

| Match | % Difference | Length | Library Entry Name |
|---|---|---|---|
| 1 | 0.19 | 535 | *Bacillus subtilis* ssp. *subtilis* |
| 2 | 0.84 | 535 | *Bacillus atrophaeus* |
| 3 | 1.03 | 535 | *Bacillus amyloliquifaciens* |

2.1.2.2 Results of FAME Analysis Comparison

| S. No. | Similarity Index | Library Entry Name |
|---|---|---|
| 1 | 0.827 | *Bacillus subtilis* |
| 2 | 0.749 | *Bacillus atrophaeus* |

The isolated bacterium is a new member of the genus *Bacillus*. According to bacterial nomenclature convention, the novel bacterial species was named as *Bacillus subtilis* ssp. *shriramensis*. The bacterium is deposited in the Microbial Type Culture Collection (MTCC) at IMTECH, Chandigarh, India. The deposition number of this novel species is (MTCC-5674).

Example 3

3.1 Production and Screening of the Antimicrobial and/or Antifungal Agent 3.1.1 Production of Antimicrobial and/or Antifungal Agent Material
T3 broth—1 L
Conical Flask—2 L capacity
Kanamycin (30 µg/ml)
*Bacillus subtilis* ssp. *shriramensis* (MTCC-5674) inoculum
Shaking Incubator (set at 30° C. temperature & 200 rpm shaking)

Method
The T3 broth was prepared according the method described in Annexure-I (1). A 1 ml culture of *Bacillus subtilis* ssp. *shriramensis* (MTCC-5674) was inoculated into the sterile T3 broth and incubated in the shaking incubator at 30° C. for 60 hours, while shaking at 200 rpm. Followed by the growth of *Bacillus subtilis* ssp. *shriramensis* (MTCC-5674) in the T3 broth for 60 hours, the culture medium was centrifuged at 12000 rpm and 4° C. for 10 min. The supernatant was collected and passed through 0.22 µm filters to separate out any residual bacterial cells. The filtrate was maintained at 4° C.

3.1.2 Screening the Antimicrobial and/or Antifungal Activity of the Culture Filtrate Collected in Step 3.1.1 Above Material
Culture Filtrate of *Bacillus subtilis* ssp. *shriramensis* (MTCC-5674) containing antimicrobial and/or antifungal agent
PDA plates
Test fungus *Fusarium oxysporum*
Incubator Method
To test the activity of antimicrobial and/or antifungal agent in the filtrate, a well was made in one corner of the PDA agar plate, 500 µl of the filtrate was placed in the well. A loop full of the fungus *Fusarium oxysporum* was inoculated at the other corner in the same PDA agar plate and incubated for 5 days at room temperature. Inhibitory activities of the filtrate against the fungus *Fusarium oxysporum* were recorded as the inhibitory zone surrounding the well in millimetres.

Result
Clear inhibitory zone of 14 mm was observed surrounding the well, suggesting that the method used for the production of antimicrobial and/or antifungal agent is optimum.

3.2 Characterization of Antimicrobial and/or Antifungal Agent

The antimicrobial and/or antifungal activity associated with *Bacillus subtilis* ssp. *shriramensis* was investigated to ascertain the nature of agent causing antimicrobial and/or antifungal activity.

Material
T3 broth—1 L
Conical Flask—2L capacity
Kanamycin (30 µg/ml)
*Bacillus subtilis* ssp. *shriramensis* (MTCC-5674) inoculum
Shaking Incubator Method
The T3 broth was prepared according the method described in Annexure-I (1). A 1 ml aliquot of 24 hours old *Bacillus subtilis* ssp. *shriramensis* (MTCC-5674) was inoculated into the sterile T3 broth and incubated in the shaking incubator at 30° C. for 60 hours, while shaking at 200 rpm. Following growth of *Bacillus subtilis* ssp. *shriramensis* (MTCC-5674) in the T3 broth for 60 hours, the culture medium was centrifuged at 12000 rpm and 4° C. for 10 min. The supernatant was collected and passed through 0.22 µm filters to remove any remaining bacterial cells.

3.2.1 Antimicrobial and/or Antifungal Assay with the *Bacillus subtilis* ssp. *shriramensis* (MTCC-5674) Bacterial Cells To test the activity of antimicrobial and/or antifungal agent by the cells, a loop full of *Bacillus subtilis* ssp. *shriramensis* (MTCC-5674) inoculated in one corner of the T3 agar plate and a loop full of the fungus *Fusarium oxysporum* was inoculated at the other corner in the same T3 agar plate and incubated for 5 days at room temperature. Inhibitory activities of the bacterial cells against the fungus *Fusarium oxysporum* were recorded as the inhibitory zone surrounding the bacterial colony in millimetres.

Result
Clear inhibitory zone of 14 mm (FIG. 11A) was observed surrounding the bacterial colony, suggesting that the active compound secreted by the bacterial cells is getting diffused out in the culture medium resulting in clearance zone away from bacterial colony.

3.2.2 ANTIMICROBIAL and/or Antifungal Assay with the *Bacillus subtilis* ssp. *shriramensis* (MTCC-5674) Culture Filtrate To test the nature of antimicrobial and/or antifungal agent in the filtrate, a well was made in the PDA agar plate and 500 µl of the filtrate was placed in the well. A loop full of the fungus *Fusarium oxysporum* was inoculated at the diagonally opposite end of the same PDA agar plate and incubated for 5 days at room temperature. Inhibitory activities of the filtrate against the fungus

*Fusarium oxysporum* were recorded as the inhibitory zone surrounding the well in millimetres.

Result

Clear inhibitory zone of 14 mm (FIG. 11B) was observed surrounding the well, suggesting that the filtrate retained antimicrobial and/or antifungal activity, thus indicating the active compound is secreted outside the bacterial cell in to the culture medium.

3.3 Determination of MIC of *Bacillus subtilis* ma. *shriramensis* (MTCC-5674 Antimicrobial and/or Antifungal Agent 3.3.1 Lyophilization of Antimicrobial and/or Antifungal Agent Material Culture filtrate of *Bacillus subtilis* ssp. *shriramensis* (MTCC-5674)

Ammonium sulphate

Freeze drier

Method

The antimicrobial and/or antifungal agent was produced and purified by the methods explained in 3.1.1. A 800 ml aliquot culture filtrate was mixed with 382.18 g ammonium sulphate at 70% (w/v) saturation (modified protocol of Jing et al., 2009) and solution was gently mixed by stirring for overnight at 4° C. The suspension was centrifuged at 10,000 rpm for 10 min at 4° C. The pellet thus obtained was lyophilized for 24 hours in a freeze drier and the dried pellet was stored at room temperature.

3.3.2 MIC of *Bacillus subtilis* ssp. *shriramensis* (MTCC-5674) Antimicrobial and/or Antifungal Agent Methods 3.3.2.1 Tube Dilution Method 3.3.2.2 Agar Diffusion Method Preparation of Stock Solution of Lyophilized Antimicrobial and/or Antifungal Agent The stock solution was prepared by dissolving 1 g of lyophilized powder of antimicrobial and/or antifungal agent in 50 ml phosphate buffer (pH 7.0). The final concentration of the stock solution was adjusted to 20 µg/µl. This stock solution was used for making dilutions with PDB media in different ratios as shown in Table-1.

3.3.2.1 Tube Dilution Method

Material 1.5 ml tubes

PDB medium

Antimicrobial and/or antifungal agent stock

*Fusarium oxysporum* spore suspension

Method

MIC assay of antimicrobial and/or antifungal agent was carried out in 1.5 ml tubes. Different dilutions of antimicrobial and/or antifungal agent were prepared in PDB medium (Table-2) ranging from 10 µg/µl (1:1) to 198 ng/µl (1:100). The MIC assay was carried out against *Fusarium oxysporum* by adding 30 µl (5×10$^6$ cfu/ml) of spore suspension in all the tubes and were incubated at 28° C., for 2 days, shaking at 180 rpm.

Three controls were used, one with undiluted antimicrobial and/or antifungal agent stock, second with 70% ammonium sulfate in PDB and third with only PDB. Medium in all the three tubes was inoculated with 30 µl (5×10$^6$ cfu/ml) of *Fusarium oxysporum* spores suspension and were incubated at 28° C., for 2 days, while shaking at 180 rpm.

3.3.2.2 Agar Diffusion Method

Material

PDA (Potato Dextrose Agar) plates

PDB (Potato Dextrose Broth) medium

Antimicrobial and/or antifungal agent stock

*Fusarium oxysporum*

Method

MIC assay of lyophilized *Bacillus subtilis* ssp. *shriramensis* (MTCC-5674) antimicrobial and/or antifungal agent was also carried out by agar diffusion method. Four wells of 9 mm diameter each were made at equal distances in PDA plates. Different dilutions of antimicrobial and/or antifungal agent were prepared in PDB (Table-3) ranging from 10 µg (1:1) to 198 ng (1:100). An aliquot 200 µl of each dilution was place in to the well labeled with the respective dilution. The test fungus *Fusarium oxysporum* was inoculated in the center of the PDA medium and the plates were incubated at 28° C. for 4 days.

A plate with three controls, one containing undiluted antimicrobial and/or antifungal agent stock, the second containing only PDB broth and the third containing PDB with 70% ammonium sulphate was used as control. The activity was measured as inhibitory zone in millimeters surrounding the well.

Result

Tube Dilution Method (FIG. 12)

The samples were observed after 48 hours of incubation under light microscope for spore germination. Spores did not germinate in the tubes containing antimicrobial and/or antifungal agent in the ratios 1:1, 1:2, 1:3 and 1:4. Moderate spore germination was observed in the tubes containing antimicrobial and/or antifungal agent in the ratios 1:5, 1:6, 1:7, 1:8 and 1:9 dilutions, and normal spore germination and mycelia formation was observed in the remaining tubes containing the antimicrobial and/or antifungal agent in the ratios 1:10 to 1:100 (Table 2).

TABLE 2

MIC of antimicrobial and/or antifungal agent by tube dilution method

| S. No. | Antimicrobial and/or antifungal agent:PDB | Concentration of antimicrobial and/or antifungal agent after dilution (µg/µl) | Total concentration of antimicrobial and/or antifungal agent used per well in agar plate (µg/200 µl) | Percent of fungus inhibited (inhibition zone in mm) |
|---|---|---|---|---|
| 1 | 1:1 | 10.000 | 2000.00 | 92.30 (12) |
| 2 | 1:2 | 6.666 | 1333.20 | 84.61 (11) |
| 3 | 1:3 | 5.000 | 1000.00 | 76.92 (10) |
| 4 | 1:4 | 4.000 | 800.00 | 61.53 (8) |
| 5 | 1:5 | 3.333 | 666.60 | 46.15 (6) |
| 6 | 1:6 | 2.857 | 571.40 | 38.46 (5) |

TABLE 2-continued

MIC of antimicrobial and/or antifungal agent by tube dilution method

| S. No. | Antimicrobial and/or antifungal agent:PDB | Concentration of antimicrobial and/or antifungal agent after dilution (µg/µl) | Total concentration of antimicrobial and/or antifungal agent used per well in agar plate (µg/200 µl) | Percent of fungus inhibited (inhibition zone in mm) |
|---|---|---|---|---|
| 7 | 1:7 | 2.500 | 500.00 | 23.07 (3) |
| 8 | 1:8 | 2.222 | 444.40 | 15.38 (2) |
| 9 | 1:9 | 2.000 | 400.00 | 0 (0) |
| 10 | 1:10 | 1.818 | 363.60 | 0 (0) |
| 11 | 1:15 | 1.250 | 250.00 | 0 (0) |
| 12 | 1:20 | 0.952 | 190.40 | 0 (0) |
| 13 | 1:25 | 0.769 | 153.80 | 0 (0) |
| 14 | 1:30 | 0.645 | 129.00 | 0 (0) |
| 15 | 1:35 | 0.555 | 111.00 | 0 (0) |
| 16 | 1:40 | 0.487 | 97.40 | 0 (0) |
| 17 | 1:45 | 0.434 | 86.80 | 0 (0) |
| 18 | 1:50 | 0.392 | 78.40 | 0 (0) |
| 19 | 1:55 | 0.357 | 71.40 | 0 (0) |
| 20 | 1:60 | 0.327 | 65.40 | 0 (0) |
| 21 | 1:65 | 0.303 | 60.60 | 0 (0) |
| 22 | 1:70 | 0.281 | 56.20 | 0 (0) |
| 23 | 1:75 | 0.263 | 52.60 | 0 (0) |
| 24 | 1:80 | 0.246 | 49.20 | 0 (0) |
| 25 | 1:85 | 0.232 | 46.40 | 0 (0) |
| 26 | 1:90 | 0.219 | 43.80 | 0 (0) |
| 27 | 1:95 | 0.208 | 41.60 | 0 (0) |
| 28 | 1:100 | 0.198 | 39.60 | 0 (0) |
| 29 | Only antimicrobial and/or antifungal agent | Crude (20 µg/µl) | 4000.00 | 100 (13) |
| 30 | Only PDB medium | 0 | 0 | 0 (0) |
| 31 | Only ammonium sulphate 70% | 0 | 0 | 0 (0) |

Agar Diffusion Method (FIG. 31)

Inhibition of fungal mycelium growth was observed around the wells containing antimicrobial and/or antifungal agent in the ratios 1:1, 1:2, 1:3 and 1:4 (Table 3). Moderate inhibition was observed surrounding the wells containing antimicrobial and/or antifungal agent in the ratios 1:5, 1:6 and 1:7 dilutions and no inhibition were observed in the remaining dilutions (from 1:8 to 1:100) (Table 3).

Conclusion

From the above experiment it is concluded that the antimicrobial and/or antifungal agent in powder of crude extract is inhibiting spore germination as well as mycelium growth upto a dilution of 1:4 (v/v), in a concentration dependent manner.

TABLE 3

MIC of antimicrobial and/or antifungal agent by agar diffusion method

| S. No. | Antimicrobial and/or antifungal agent:PDB | Concentration of antimicrobial and/or antifungal agent after dilution (µg/µl) | Total concentration of antimicrobial and/or antifungal agent used per tube (µg/200 µl) | Spore germination |
|---|---|---|---|---|
| 1 | 1:1 | 10.000 | 2000.00 | No germination |
| 2 | 1:2 | 6.666 | 1333.20 | No germination |
| 3 | 1:3 | 5.000 | 1000.00 | No germination |
| 4 | 1:4 | 4.000 | 800.00 | No germination |
| 5 | 1:5 | 3.333 | 666.60 | Germ tube emergence |
| 6 | 1:6 | 2.857 | 571.40 | Germ tube growth |
| 7 | 1:7 | 2.500 | 500.00 | Germ tube elongation |
| 8 | 1:8 | 2.222 | 444.40 | Mycelia growth |
| 9 | 1:9 | 2.000 | 400.00 | Mycelia extension |
| 10 | 1:10 | 1.818 | 363.60 | Compact mycelia |
| 11 | 1:15 | 1.250 | 250.00 | Compact mycelia |
| 12 | 1:20 | 0.952 | 190.40 | Compact mycelia |
| 13 | 1:25 | 0.769 | 153.80 | Compact mycelia |
| 14 | 1:30 | 0.645 | 129.00 | Compact mycelia |
| 15 | 1:35 | 0.555 | 111.00 | Compact mycelia |
| 16 | 1:40 | 0.487 | 97.40 | Compact mycelia |
| 17 | 1:45 | 0.434 | 86.80 | Compact mycelia |
| 18 | 1:50 | 0.392 | 78.40 | Compact mycelia |

TABLE 3-continued

MIC of antimicrobial and/or antifungal agent by agar diffusion method

| S. No. | Antimicrobial and/or antifungal agent:PDB | Concentration of antimicrobial and/or antifungal agent after dilution (μg/μl) | Total concentration of antimicrobial and/or antifungal agent used per tube (μg/200 μl) | Spore germination |
|---|---|---|---|---|
| 19 | 1:55 | 0.357 | 71.40 | Compact mycelia |
| 20 | 1:60 | 0.327 | 65.40 | Compact mycelia |
| 21 | 1:65 | 0.303 | 60.60 | Compact mycelia |
| 22 | 1:70 | 0.281 | 56.20 | Compact mycelia |
| 23 | 1:75 | 0.263 | 52.60 | Compact mycelia |
| 24 | 1:80 | 0.246 | 49.20 | |
| 25 | 1:85 | 0.232 | 46.40 | Compact mycelia |
| 26 | 1:90 | 0.219 | 43.80 | Compact mycelia |
| 27 | 1:95 | 0.208 | 41.60 | Compact mycelia |
| 28 | 1:100 | 0.198 | 39.60 | Compact mycelia |
| 29 | Only antimicrobial and/or antifungal agent | Crude (20 μg/μl) | 4000.00 | No germination |
| 30 | Only PDB | 0 | 0 | Compact mycelia |
| 31 | Only ammonium sulphate 70% | 0 | 0 | Compact mycelia |

3.4 to Test the Antimicrobial and/or Antifungal Activity of Cell Lysate of the Novel Isolate *Bacillus subtilis* ssp. *shriramensis* (MTCC-5674)

Material

PDA agar plates

LB Broth

*Bacillus subtilis* ssp. *shriramensis* (MTCC-5674) cells

Lysozyme

Incubator

Methods 3.4.1 *Bacillus subtilis* ssp. *shriramensis* (MTCC-5674) Cell Lysis

The LB broth was prepared according to the method described in Annexure-I (3). A single colony of *Bacillus subtilis* ssp. *shriramensis* (MTCC-5674) was inoculated into the sterile LB broth and incubated at 30° C. for 24 hours. After 24 hours of incubation the vegetative cells were collected by centrifugation at 6500 rpm, 4° C., the cells were washed thrice with sterile distilled water and subjected to cell lysis by incubation in lysozyme at 37° C. for 2 h. After lysis the suspension was centrifuged at 10,000 rpm for 10 min at 4° C. to remove the cell debris. The supernatant was collected and passed through 0.22 μm filter and stored at 4° C.

3.4.2 Antimicrobial and/or Antifungal Assay of the Cell Lysate

Two wells were bored in two diagonal ends of the PDA agar in the petri plate and labelled one as "test" and the other as "control". An aliquot of 500 μl of the lysate was added to the test well and 500 μl of only lysozyme was added to the control well. The test fungus *Fusarium oxysporum* was inoculated in the middle of the PDA agar and incubated for 5 days at room temperature.

Result

The cell lysate did not exhibit antimicrobial and/or antifungal activity (FIG. 15) against the fungus *Fusarium oxysporum*, suggesting that the antimicrobial and/or antifungal agent is primarily secreted out into the media.

Example 4

4.1 to Test the Antimicrobial and/or Antifungal Activity Against Other Pathogenic Fungi Material

*Bacillus subtilis* ssp. *shriramensis* (MTCC-5674)

Plant Pathogenic fungi

1. *Rhizoctonia solani* (Causes sheath blight in members of family solanacea).
2. *Sarocladium oryzae* (Causes sheath rot in rice)
3. *Colletotrichum capsicii* (Causes anthracnose in chilli).
4. *Exerohilum turcicum* (Causes turcicum blight).
5. *Macrophomina phaseolina* (Causes charcoal rot).

T3—broth

T3—Agar plates

PDA—Agar plates

Incubator

Method 4.1.1 to Test the Antimicrobial and/or Antifungal Activity with *Bacillus subtilis* Ssp. *shriramensis* (MTCC-5674) Cells Against Various Plant Pathogenic Fungi A loop full of *Bacillus subtilis* ssp. *shriramensis* (MTCC-5674) cells and a loop full of test fungi were inoculated at the diagonally opposite ends of the T3 plates labeled with the respective fungus and incubated at 28° C. till the growth of fungal mycelium was observed in the vicinity of the bacterial colony.

4.1.2 to Test the Antimicrobial and/or Antifungal Activity with the Filtrate Against Various Plant Pathogenic Fungi An aliquot of 500 μl of the culture filtrate containing antimicrobial and/or antifungal agent was added into the wells made in the PDA agar and a loop full of test fungi were inoculated at the other corner of the respective plates labeled with the respective fungus and incubated at 28° C. till the growth of fungal mycelium was observed in the vicinity of the well containing culture filtrate.

The inhibitory activity of the filtrate against the target fungus was recorded in millimetres as the inhibitory zone formed surrounding the well.

Result

A range of fungal species causing diseases in plants were tested in the antimicrobial and/or antifungal assay and all of them demonstrated complete inhibition of growth in the presence of *Bacillus subtilis* ssp. *shriramensis* (MTCC-5674) cells and also its culture filtrate.

4.2 Efficacy of Antimicrobial and/or Antifungal Agent in Protecting Rice Seed from Fungal Attack Rice seeds were treated with *Fusarium oxysporum* spores and *Bacillus subtilis* ssp. *shriramensis* (MTCC-5674) culture filtrate and placed in the petri plates containing plain agar to check the efficacy of *Bacillus subtilis* ssp. *shriramensis* (MTCC-5674) antimicrobial and/or antifungal agent in inhibiting the fungal attack on germinating seed.

Control seeds were treated only with *Fusarium oxysporum* fungal spores.

Result

In presence of *Bacillus subtilis* ssp. *shriramensis* (MTCC-5674) antimicrobial and/or antifungal agent fungus failed to infect the seeds and the rice seeds germinated normally. However, the seeds treated only with fungus showed severe infection and failed to germinate (FIG. 17).

4.3 to Test the Pathogenic Nature of *Bacillus subtilis* ssp. *shriramensis* (MTCC-5674) of Plants Material

*Bacillus subtilis* ssp. *shriramensis* (MTCC-5674) in 1% CMC in sprayable form

Rice, cotton, tobacco, corn and tomato plants

Sprayer

Method

The *Bacillus subtilis* ssp. *shriramensis* (MTCC-5674) culture was extensively tested for pathogenic behaviour if any, on a range of plant species.

*Bacillus subtilis* ssp. *shriramensis* (MTCC-5674) was inoculated into 1 L sterile LB broth in a 2 L conical flask and incubated at 30° C., for 24 hours, shaking at 200 rpm. Following the growth of the bacteria, the cells were harvested by centrifuging at 6,500 rpm, at 4° C. for 10 min. The pellet was washed twice in phosphate buffer (pH 7.0) and made into slurry in 1% CMC (Carboxy Methyl Cellulose) in phosphate buffer (pH 7.0). This suspension was used for spraying on crop plants like rice, tobacco, corn, tomato and cotton.

Result

From the observations it has been concluded that, all the plant species (rice, tobacco, corn, tomato and cotton) sprayed with *Bacillus subtilis* sp. *shriramensis* (MTCC-5674) did not exhibit any kind of disease symptoms and their growth and development was equivalent to control plants indicating that *Bacillus subtilis* ssp. *shriramensis* (MTCC-5674) is non-pathogenic for plant species (FIG. 18).

Example 5

5.1 Formulation of Antimicrobial and/or Antifungal Compositions Containing *Bacillus subtilis* ssp. *shriramensis* (MTCC-5674) Cells as a Biological Control Agent Material

*Bacillus subtilis* ssp. *shriramensis* (MTCC-5674)
LB—broth
PDB (Potato Dextrose Broth)
Phosphate buffer (pH 7.0)
CMC (Carboxy Methyl Cellulose)

Method 5.1.1 Preparation of *Bacillus subtilis* ssp. *shriramensis* (MTCC-5674) Cell Suspension

*Bacillus subtilis* ssp. *shriramensis* (MTCC-5674) was Inoculated in 1 L Sterile LB broth in a 2 L conical flask and incubated at 30° C., for 24 hours, shaking at 200 rpm. Following the growth *Bacillus subtilis* ssp. *shriramensis* (MTCC-5674), the culture was centrifuged at 6,500 rpm, at 4° C. for 10 min. The pellet was washed twice in phosphate buffer (pH 7.0) and mixed with 1% CMC (Carboxy Methyl Cellulose) in phosphate buffer (pH 7.0) to prepare a slurry containing $6 \times 10^7$ cfu/ml. The slurry containing *Bacillus subtilis* ssp. *shriramensis* (MTCC-5674) was used to spray on plants and treat plant seedling roots by dipping.

5.1.2 to Test the Efficacy of Formulate Containing Antimicrobial and/or Antifungal Agent to Inhibit the Infestation of *Rhizoctonia solani* (NFCCI-3194) in the Roots of Tomato Material Slurry containing *Bacillus subtilis* ssp. *shriramensis* (MTCC-5674)

*Rhizoctonia solani* (NFCCI-3194) fungus (causes sheath blight in members of family solanacea).

Soil rite

Tomato seedlings 5.1.3 Preparation of *Rhizoctonia solani* (NFCCI-3194)

*Rhizoctonia solani* (NFCCI-3194) was grown in Potato Dextrose Broth (prepared as per the method provided in the Annexure-I (V) medium for 6 days. Following the growth of the *Rhizoctonia solani* (NFCCI-3194), it was thoroughly mixed with soil rite and incubated for 15 days at room temperature. The soil rite containing the fungus was mixed with soil in 1:1 ratio.

Tomato Seedlings

Tomato seedlings of 10 cm height were used in this study

Method

The experiment was carried out as described below

A. Tomato seedlings were planted in the soil containing *Rhizoctonia solani* (NFCCI-3194), but were not treated with *Bacillus subtilis* sop. *shriramensis* (MTCC-5674).

B. The roots of Tomato seedlings were treated with slurry containing *Bacillus subtilis* ssp. *shriramensis* (MTCC-5674) and were planted in the soil containing *Rhizoctonia solani* (NFCCI-3194).

C. Tomato seedlings without any treatment.

A. Seedling Treatment with *Bacillus subtilis* sap. *shriramensis* (MTCC-5674) Cells and Fungus *Rhizoctonia solani* (NFCCI-3194)

Tomato seedling roots were dipped in the *Bacillus subtilis* ssp. *shriramensis* (MTCC-5674) cell formulate for 30 min. The treated seedlings were planted hi the pot containing soil mixed with the fungus *Rhizoctonia solani* (NFCCI-3194).

Control Seedlings

For inducing the disease in the seedlings, tomato seedlings (untreated) were planted in the pot containing soil mixed with the fungus *Rhizoctonia solani* FCC-3194.

For negative control tomato seedlings (untreated) were planted in poi containing soil which is not mixed with the fungus *Rhizoctonia solani* (NFCCI-3194).

All the pots containing tomato seedlings were transferred to the green house and maintained till fruiting stage.

Result

From the observations it was concluded that the seedlings treated with combination of *Bacillus subtilis* ssp. *shriramensis* (MTCC-5674) and the fungus *Rhizoctonia solani* (NFCCI-3194) grew very well equivalent to control plants, whereas the seedlings (untreated) planted in the pot containing fungus *Rhizoctonia solani* (NFCCI-3194) exhibited retarded growth, poor flowering and fruit formation as compared with control. Hence, it can been concluded that *Bacillus subtilis* ssp. *shriramensis* (MTCC-5674) inhibited the growth of the fungus *Rhizoctonia solani* (NFCCI-3194) in the rhizosphere area of tomato seedlings and protected the seedlings from disease causing fungus (FIG. 19).

Example 6

6.1 In vitro Evaluation of Minimum Number of *Bacillus subtilis* ssp. *shriramensis* (MTCC-5674) Cells which can Control the Infection of Germinating Corn Seeds by Soil and Seed Borne Fungal Pathogen *Penicillium oxalicum* (NFCCI-1997).

6.1.1 Preparation of Bacterial and Fungal Suspension Cultures

Materials a. *Bacillus subtilis* ssp. *shriramensis* (MTCC-5674)
b. *Penicillium oxalicum* (NFCCI-1997)—Plant pathogenic fungus
c. Carbendazim WP50 (commercial fungicide)
d. Luria Bertani Broth (LB)

Method 6.1.1.1 Preparation of Suspension Culture of *Bacillus subtilis* ssp. *shriramensis* (MTCC-5674)

A pure colony of *Bacillus subtilis* ssp. *shriramensis* (MTCC-5674) (FIG. 20-1) was inoculated in 10 ml LB broth and incubated at 30° C. for 24 h at 180 rpm. For preparation of bio-control formulation 1 ml of fresh culture was inoculated in 100 ml of LB broth and incubated at 30° C. for 24 h at 180 rpm. Growth of culture was monitored by periodic measurement of absorbance of culture at 625 nm. The bacterial cells were harvested by centrifugation and washed with sterile phosphate buffer, by centrifugation at 5500 rpm for 10 min at 4° C. The cells were finally suspended in 5 ml of sterile phosphate buffer. This concentrated suspension was used for preparation of bio-control formulations.

6.1.1.2 Preparation of Suspension Culture of *Penicillium oxalicum* (NFCCI-1997) (Fungal Pathogen)

Pure colony of *Penicillium oxalicum* (NFCCI-1997) (FIG. 20-2) was inoculated on PDA plate and incubated at 28° C. till spore formation. A loop full of the fungal spores were inoculated in 100 ml of PDB and incubated at 28° C. for 7 days at 180 rpm. The aqueous part of the culture containing fungal spores was collected in 50 ml polypropylene tubes. The spores were washed with sterile phosphate buffer by centrifugation at 8000 rpm for 10 min at 4° C. The spores were suspended in required volume of sterile phosphate buffer to obtain a cfu of $6 \times 10^4$ $ml^{-1}$.

6.1.2 Soil Infestation with *P. oxalicum* (NFCCI-1997) (Fungal Pathogen)

To maintain adequate fungal spore load in the soil medium, 50 ml fungal spore suspension ($6 \times 10^4$ cfu/ml) was mixed with 1 kg of autoclaved soilrite and incubated for 10 days at 28° C. The soilrite colonized with fungus was uniformly mixed with soil in 1:1 ratio and filled in 96 cup trays.

6.1.3 Preparation of Formulation of *Bacillus subtilis* ssp. *shriramensis* (MTCC-5674) for Biological Control of Soil Borne Plant Disease Material a. CMC (Carboxy Methyl Cellulose)
b. Sucrose
c. Red polymer (without fungicide)
d. *Bacillus subtilis* ssp. *shriramensis* (MTCC-5674) cell suspension (bio-control agent)
e. Carbendazim (commercial fungicide)

To assess effective concentration of *Bacillus subtilis* ssp. *shriramensis* (MTCC-5674) cells which can suppress growth and pathogenicity of *P. oxalicum* (NFCCI-1997) on germinating corn seed, four different formulations were designed (details are provided in table below). Formulations containing only bio-control agent, only commercial fungicide, and one without bio-control agent or fungicide were used as controls. All the formulations contain a binding material—CMC (Carboxy Methyl Cellulose), carbon source (sucrose) and a red polymer (without fungicide).

1. Control-1 (Formulation without Fungal Pathogen and Bio-Control Agent)

This formulation is composed of 1% CMC, 2% sucrose, and red polymer. This formulation has no bio-control agent, disease causing agents and fungicide. Seeds treated with this formulation were used as control seeds.

Composition

| S. No. | Components | Weight/Volume/Number | Final Concentration |
|---|---|---|---|
| 1 | CMC | 1.71 µg | 1.00% w/v |
| 2 | Sucrose | 3.42 µg | 2.00% w/v |
| 3 | Red Polymer | 34 µl | 19.88% v/v |
| 4 | Water | 31.87 µl | — |
| | Total | 171 µl | — |

2. Control-2 (Formulation with Fungal Pathogen but No Bio-Control Agent)

This formulation is composed of 1% CMC, 2% sucrose, and red polymer. It has no bio-control agent/commercial fungicide, but the seeds treated with this formulation were sown in the soil inoculated with *P. oxalicum* (NFCCI-1997) fungus. As there is no biological or chemical protection around the seeds, the fungus grows profusely, infects the seeds and develops disease in the seedlings. The seeds treated with this formulation are used as diseased controls.

Composition

| S. No. | Components | Weight/Volume/Number | Final concentration |
|---|---|---|---|
| 1 | *P. oxalicum* (NFCCI-1997) | Present in the soil | — |
| 2 | CMC | 1.71 µg | 1.00% w/v |
| 3 | Sucrose | 3.42 µg | 2.00% w/v |
| 4 | Red Polymer | 34 µl | 19.88% v/v |
| 5 | Water | 31.87 µl | — |
| | Total | 171 µl | — |

3. Control-3 (Formulation with Commercial Fungicide "Carbendazim WP50").

This formulation is composed of 1% CMC, 2% sucrose, red polymer and a commercial fungicide Carbendazim WP50 (trade name Bavistin) was used at a concentration of 500 µg/ml (Mohiddin at al., 2013). This formulation is used to compare the efficacies of both biocontrol agent and the commercial fungicide in suppressing the fungal growth in the vicinity of the germinating seed.

Composition

| S. No. | Components | Weight/Volume/Number | Final concentration |
|---|---|---|---|
| 1 | Carbendazim | 85.50 µg | |
| 2 | CMC | 1.71 µg | 1.00% w/v |
| 3 | Sucrose | 3.42 µg | 2.00% w/v |
| 4 | Red Polymer | 34 µl | 19.88% v/v |
| 5 | Water | 31.87 µl | — |
| | Total | 171 µl | — |

4a. Formulation with *Bacillus subtilis* ssp. *shriramensis* (MTCC-5674) ($5\times10^4$ cfu)

This formulation is composed of 1% CMC, 2% sucrose, red polymer and *Bacillus subtilis* ssp. *shriramensis* (MTCC-5674) cells at a concentration of $5\times10^4$ cfu/ml. This formulation has minimum number of *Bacillus subtilis* sp. *shriramensis* (MTCC-5674) cells.

Composition

| S. No. | Components | Weight/Volume/Number | Final concentration |
|---|---|---|---|
| 1 | *Bacillus subtilis* ssp. *shriramensis* (MTCC-5674) cell suspension | 100.00 µl | $5 \times 10^4$ cfu/ml |
| 2 | CMC | 1.71 µg | 1.00% w/v |
| 3 | Sucrose | 3.42 µg | 2.00% w/v |
| 4 | Red Polymer | 34.0 µl | 19.88% v/v |
| 5 | Water | 31.87 µl | — |
| | Total | 171.0 µl | — |

4b. Formulation with *Bacillus subtilis* ssp. *shriramensis* (MTCC-56741 cells ($5\times10^5$ cfu)

This formulation is composed of 1% CMC, 2% sucrose, red polymer and *Bacillus subtilis* ssp. *shriramensis* (MTCC-5674) cells at a concentration of $5\times10^5$ cfu/ml.

Composition

| S. No. | Components | Weight/Volume/Number | Final concentration |
|---|---|---|---|
| 1 | *Bacillus subtilis* ssp. *shriramensis* (MTCC-5674) cell suspension | 100.00 µl | $5 \times 10^5$ cfu/ml |
| 2 | CMC | 1.71 µg | 1.00% w/v |
| 3 | Sucrose | 3.42 µg | 2.00% w/v |
| 4 | Red Polymer | 34 µl | 19.88% v/v |
| 5 | Water | 31.87 µl | — |
| | Total | 171 µl | — |

4c. Formulation with *Bacillus subtilis* ssp. *shriramensis* (MTCC-5674) cells ($5\times10^6$ cfu)

This formulation is composed of 1% CMC, 2% sucrose, red polymer and *Bacillus subtilis* ssp. *shriramensis* (MTCC-5674) cells at a concentration of $5\times10^6$ cfu/ml.

Composition

| S. No. | Components | Weight/Volume/Number | Final concentration |
|---|---|---|---|
| 1 | *Bacillus subtilis* ssp. *shriramensis* (MTCC-5674) cell suspension | 100.00 µl | $5 \times 10^6$ cfu/ml |
| 2 | CMC | 1.71 µg | 1.00% w/v |
| 3 | Sucrose | 3.42 µg | 2.00% w/v |
| 4 | Red Polymer | 34 µl | 19.88% v/v |
| 5 | Water | 31.87 µl | — |
| | Total | 171 µl | — |

4d. Formulation containing *Bacillus subtilis* ss. *shriramensis* cells ($5\times10^7$ cfu)

This formulation is composed of 1% CMC, 2% sucrose, red polymer and *Bacillus subtilis* ssp. *shriramensis* (MTCC-5674) cells at a concentration of $5\times10^7$ cfu/ml (50 million cells/ml of carrier). This formulation has maximum number of *Bacillus subtilis* ssp. *shriramensis* (MTCC-5674) cells.

Composition

| S. No. | Components | Weight/Volume/Number | Final concentration |
|---|---|---|---|
| 1 | *Bacillus subtilis* ssp. *shriramensis* (MTCC-5674) cell suspension | 100.00 µl | $5 \times 10^7$ cfu/ml |
| 2 | CMC | 1.71 µg | 1.00% w/v |
| 3 | Sucrose | 3.42 µg | 2.00% w/v |
| 4 | Red Polymer | 34 µl | 19.88% v/v |
| 5 | Water | 31.87 µl | — |
| | Total | 171 µl | — |

5. Formulation with Only *Bacillus subtilis* ssp. *shriramensis* (MTCC-5674) Cells ($5\times10^7$ cfu)

This formulation is composed of 1% CMC, 2% sucrose, red polymer and *Bacillus subtilis* ssp. *shriramensis* (MTCC-5674) cells at a concentration of $5\times10^7$ cfu/ml. This formulation has maximum number of *Bacillus subtilis* ssp. *shriramensis* (MTCC-5674) cells and is used to study the effect of biocontrol agent on seed germination and plant growth.

Composition

| S. No. | Components | Weight/Volume/Number | Final Concentration |
|---|---|---|---|
| 1 | *Bacillus subtilis* ssp. *shriramensis* (MTCC-5674) cell suspension | 100.00 µl | $5 \times 10^7$ cfu/ml |
| 2 | CMC | 1.71 µg | 1.00% w/v |
| 3 | Sucrose | 3.42 µg | 2.00% w/v |
| 4 | Red Polymer | 34 µl | 19.88% v/v |
| 5 | Water | 31.87 µl | — |
| | Total | 171 µl | — |

TABLE 4

Experiment plan in tabular form

| Treatment | Material used | *Bacillus subtilis* ssp. *shriramensis* (MTCC-5674) cells (cfu/ml) | *P. oxalicum* (NFCCI-1997) spores in soil (cfu/g) | Carbendazim (in μg) | No. of corn seeds per treatment ||| 
|---|---|---|---|---|---|---|---|
| | | | | | Original | Duplicate | Triplicate |
| *1 | Corn seed + Red polymer + CMC + Sucrose (Control seed) | Nil | Nil | Nil | 20 | 20 | 20 |
| *2 | Corn seed + Red polymer + CMC + Sucrose (seed were sown in soil containing *P. oxalicum* (NFCCI-1997)) (Control seed) | Nil | $6 \times 10^4$ | Nil | 20 | 20 | 20 |
| *3 | Corn seed + Red polymer + CMC + Sucrose + Carbendazim (Control seed) | Nil | $6 \times 10^4$ | 85.50 | 20 | 20 | 20 |
| *4a | Corn seed + Red polymer + CMC + Sucrose + *Bacillus subtilis* ssp. *shriramensis* (MTCC-5674) cells (Concentration-1) | $5 \times 10^4$ | $6 \times 10^4$ | Nil | 20 | 20 | 20 |
| *4b | Corn seed + Red polymer + CMC + Sucrose + *Bacillus subtilis* ssp. *shriramensis* (MTCC-5674) cells (Concentration-2) | $5 \times 10^5$ | $6 \times 10^4$ | Nil | 20 | 20 | 20 |
| *4c | Corn seed + Red polymer + CMC + Sucrose + *Bacillus subtilis* ssp. *shriramensis* (MTCC-5674) cells (Concentration-3) | $5 \times 10^6$ | $6 \times 10^4$ | Nil | 20 | 20 | 20 |
| *4d | Corn seed + Red polymer + CMC + Sucrose + *Bacillus subtilis* ssp. *shriramensis* (MTCC-5674) cells (Concentration-4) | $5 \times 10^7$ | $6 \times 10^4$ | Nil | 20 | 20 | 20 |
| *5 | Corn seed + Red polymer + CMC + Sucrose + *Bacillus subtilis* ssp. *shriramensis* (MTCC-5674) cells | $5 \times 10^7$ | Nil | Nil | 20 | 20 | 20 |

*1 (Control-1)- Formulation without fungal pathogen and antifungal agent;
*2 (Control-2)- Formulation with fungal pathogen but no bio-control agent;
*3 (Control-3)- Formulation with commercial fungicide "Carbendazim WP50";
*4a - Formulation with *Bacillus subtilis* ssp. *shriramensis* (MTCC-5674) ($5 \times 10^4$ cfu);
*4b - Formulation with *Bacillus subtilis* ssp. *shriramensis* (MTCC-5674) cells ($5 \times 10^5$ cfu);
*4c - Formulation with *Bacillus subtilis* ssp. *shriramensis*(MTCC-5674) cells ($5 \times 10^6$ cfu);
*4d - Formulation containing *Bacillus subtilis* ssp. *shriramensis* (MTCC-5674) cells ($5 \times 10^7$ cfu) and
*5 - Formulation with only *Bacillus subtilis* ssp. *shriramensis* (MTCC-5674) cells ($5 \times 10^7$ cfu).

Seed Coating

The bio-control formulations as per the compositions given above were coated on corn seeds (FIG. 21). Twenty corn seeds in triplicates (total 60 seeds) for each treatment were surface sterilized with 0.1% $HgCl_2$ for 10 min and rinsed with 95% ethanol, and washed with sterilized water for 10 min each. Dry seeds were coated with 171 μl/60 seeds of different formulations and air dried for 2 h.

Seed Sowing

All the treated seeds were sown in 96 cup trays with three replicates per treatment. All trays were kept in glasshouse and maintained under controlled conditions. From seed germination onwards the trays were monitored till 5 weeks.

Data Recording

Germination Percentage

Germination percentage of all the seed treatments was recorded after 1 week of seed sowing.

Disease Incidence

Disease incidence was recorded as percentage after 4 weeks of seed sowing. The formula used for recording disease incidence (Hoffan et al., 2002) is as follows:

$$\% \text{ disease incidence} = \frac{\text{No. of diseased seedlings}}{\text{Total No. of seedlings}} \times 100$$

Results

Seed Germination and Seedling Survival

Optimum seed germination i.e., 93.33%, 96.66%, 100.00%, 100.00%, 100.00% and 100.00% was recorded in seeds treated with formulations—3(control-3), 4c, 1(control-1), 4b, 4d and 5, respectively, followed by 83.33% 33.33% in the seeds treated with formulations—4a and 2(control-2). The seedling survival rate after 4 weeks of sowing was recorded as 100.00% in the seeds treated with all the formulations mentioned above except in the seeds treated with the formulation-3 (which has commercial fungicide), this clearly indicates that the commercial fungicide "Carbendazim WP50", though it was efficient in suppressing fungal growth, but was not 100.00% efficient. The formulations containing different concentrations (except formulation 4a—which has least number of cells) of *Bacillus subtilis* ssp. *shriramensis* (MTCC-5674) cells proved to be 100.00% effective in protecting seeds from *P. oxalicum* (NFCCI-1997) present in the soil.

The drop in germination rate of seeds treated with formulation—4a (formulation with least concentration of bacterial cells, 50,000 cells/ml carrier) is clear indication that a basal dose of bacterial cells is required to confer protection to the germinating seeds against *P. oxalicum* (NFCCI-1997) present in the soil. Thus, formulation-4b, which has a bacterial concentration of $5 \times 10^5$ cfu/ml (0.5 million cells/ml) conferred good protection against *P. oxalicum* (NFCCI-1997) and gave 100% seed germination and seedling survival rate, same as control seeds.

TABLE 5

Detection of effective concentration (cfu/g carrier) of *Bacillus subtilis* ssp. *shriramensis* (MTCC-5674) cells for suppressing *P. oxalicum* (NFCCI-1997) growth and pathogenicity.

| Treatment | Concentration of *Bacillus subtilis* ssp. *shriramensis* (MTCC-5674) cells (cfu/g) | Concentration of *P. oxalicum* (NFCCI-1997) (cfu/ml) | Concentration of Carbendazim (µg) | No. of seed sown in tray | No. of seed germinated (Values in %) | Data recorded after 2 weeks of No. of seedlings survived (Values in %) |
|---|---|---|---|---|---|---|
| 1* | — | — | — | 60 | 60 (100%) | 60 (100%) |
| 2* | — | $6 \times 10^4$ | — | 60 | 20 (33.33%) | 0 (0%) |
| 3* | — | $6 \times 10^4$ | 85.50 | 60 | 56 (93.33%) | 54 (96.42%) |
| 4a* | $5 \times 10^4$ | $6 \times 10^4$ | — | 60 | 50 (83.33%) | 14 (28%) |
| 4b* | $5 \times 10^5$ | $6 \times 10^4$ | — | 60 | 60 (100%) | 60 (100%) |
| 4c* | $5 \times 10^6$ | $6 \times 10^4$ | — | 60 | 59 (96.66%) | 59 (100%) |
| 4d* | $5 \times 10^7$ | $6 \times 10^4$ | — | 60 | 60 (100%) | 60 (100%) |
| 5* | $5 \times 10^7$ | — | — | 60 | 60 (100%) | 60 (100%) |

| | Data recorded after 2 weeks of | | Data recorded after 4 weeks of sowing | | | |
|---|---|---|---|---|---|---|
| Treatment | No. of seedlings died because of disease (Values in %) | No. of seedlings died without disease (Values in %) | No. of seedlings survived (Values in %) | No. of seedlings died because of disease (Values in %) | No. of seedlings died without disease (Values in %) | Percentage variation (Values in %) |
| 1* | 0 | 0 | 60 (100%) | 0 | 0 | 0 |
| 2* | 20 (100%) | 0 | 0 | 0 | 0 | −100 |
| 3* | 2 (3.33%) | 0 | 54 (90%) | 0 | 0 | −10 |
| 4a* | 36 (72%) | 0 | 9 (18%) | 5 (10%) | 0 | −82 |
| 4b* | 0 | 0 | 60 (100%) | 0 | 0 | 0 |
| 4c* | 0 | 0 | 59 (100%) | 0 | 0 | 0 |
| 4d* | 0 | 0 | 60 (100%) | 0 | 0 | 0 |
| 5* | 0 | 0 | 60 (100%) | 0 | 0 | 0 |

*1 - Corn seed + red polymer + CMC + Sucrose;
*2 - Corn seed + red polymer + CMC + Sucrose + *P. oxalicum* (NFCCI-1997);
*3 - Corn seed + red polymer + CMC + Sucrose + *P. oxalicum* (NFCCI-1997) + Carbendazim;
*4a to 4d - Corn seed + red polymer + CMC + Sucrose + *P. oxalicum* (NFCCI-1997) + different concentrations of *Bacillus subtilis* ssp. *shriramensis* (MTCC. 5674) cells;
*5 - Corn seed + red polymer + CMC + Sucrose + *Bacillus subtilis* ssp *shriramensis* (MTCC-5674).

Disease Incidence

The results of the study showed that there was significant difference between the treatments. The seeds treated with the formulations 1, 4b, 4c, 4d and 5 did not exhibit any disease symptoms and displayed healthy growth, similar to control seedlings, indicating that the bio-control agent *Bacillus subtilis* ssp. *shriramensis* (MTCC-5674) present in the formulations greatly suppressed growth and pathogenicity of the fungus *P. oxalicum* (NFCCI-1997), and thus protected the seeds from getting infected with the fungus. The seeds treated with the formulation-3 (which has a commercial fungicide Carbendazim 50WP) showed a disease incidence of 3.57% indicating that though the commercial fungicide was effective in suppressing the fungal growth, but not as good as bio-control agent used in this study.

TABLE 6

Percentage disease Incidence of corn seedlings treated with different formulations.

| Treatment | Concentration of bacterial cells | Concentration of fungal spores in soil | Total No. of seedlings | No. of diseased seedlings | Percent Disease incidence |
|---|---|---|---|---|---|
| 1(control-1) | Nil | Nil | 60 | 0 | 0.00 |
| 2(control-2) | Nil | $6 \times 10^4$ | 20 | 20 | 100.00 |
| 3(control-3) | Nil | $6 \times 10^4$ | 56 | 2 | 3.57 |
| 4a | $5 \times 10^4$ | $6 \times 10^4$ | 50 | 41 | 82.00 |
| 4b | $5 \times 10^5$ | $6 \times 10^4$ | 60 | 0 | 0.00 |
| 4c | $5 \times 10^6$ | $6 \times 10^4$ | 59 | 0 | 0.00 |
| 4d | $5 \times 10^7$ | $6 \times 10^4$ | 60 | 0 | 0.00 |
| 5 | $5 \times 10^7$ | Nil | 60 | 0 | 0.00 |

Disease incidence of 82% and 100% was recorded in the seeds treated with the formulations 4a and 2, respectively. The results indicate that the *Bacillus subtilis* ssp. *shriramensis* (MTCC-5674) cell density present in the formulation 4a was not effective in suppressing growth of fungus and hence the germinating seeds were infected with the fungus and died after 2 weeks of germination. As expected, the seeds treated with formulation-2 which has neither bio-control agent nor commercial fungicide showed 100% disease Incidence indicating that the fungus infected the germinating seeds and killed the seedlings within 2 weeks of germination.

Conclusion

The above results clearly indicate that *Bacillus subtilis* ssp. *shriramensis* (MTCC-5674) at a concentration of $5 \times 10^5$ cfu/ml (formulation-4b) is effective in suppressing growth of fungal pathogen and gives 100% protection to germinating seedlings of corn. Hence, the biocontrol agent can be successfully used in coating seeds for effective control of soil borne pathogenic fungus *P. oxalicum* (NFCCI-1997).

6.2 Testing the Efficacy of the *Bacillus subtilis* ssp. *shriramensis* (MTCC-5674 Cells Formulation in Promoting the Growth and Yield in Plants Materials and Methods Materials 1. Seeds of Corn, Tomato and Brinjal treated with the formulation as mentioned in 6.1.3 (4b).
2. Control seeds of Corn, Tomato and Brinjal.

Methods

Seed Coating

Seeds of Corn, Tomato and Brinjal were treated with the formulation mentioned in 6.1.3 (4b) and air dried.

Seed Sowing

Treated and untreated (control) seeds of Corn, Tomato and Brinjal, each in three replicates and each replicate containing 23 seeds were sown in the field of 4 meters area. The standard spacing measurements like 20 cm plant to plant and 60 cm row to row distance were maintained. Appropriate agronomy practices were followed to grow these crops to maturity.

Results

There were significant increase in plant growth parameters and yield under field conditions. The seeds coated with formulate containing *Bacillus subtilis* ssp. *shriramensis* (MTCC-5674) cells increased the yield in Corn, Brinjal and Tomato by 17.60, 37.15 and 1.58%, respectively (Table-7). The Corn, Brinjal and Tomato plants showed higher rate of growth, development and biomass accumulation (a representative picture of difference in treated and untreated Corn is given in FIG. 25). Earlier reports on plant growth promoters have also proved that the formulation containing *Bacillus subtilis* enhanced the growth of plants and induced systemic resistance to disease protection by producing 60 different types of secondary metabolites (Compant et al., 2005 and Mohan Kumar et al., 2015).

TABLE 7

Effect of *Bacillus subtilis* ssp. *shriramensis* (MTCC-5674) cells formulation on the yield of Corn, Tomato and Brinjal.

| S. No. | Crop | Treatment | Yield |
|---|---|---|---|
| 1 | Corn | 1% CMC, 2% sucrose, red polymer and *Bacillus subtilis* ssp. *shriramensis* (MTCC-5674)cells at a concentration of $5 \times 10^5$ cfu/ml (0.5 million cells/ml of carrier) | 233.7 |
| | | Control | 198.72 |
| | | Increase over control | 17.60% |
| 2 | Brinjal | 1% CMC, 2% sucrose, red polymer and *Bacillus subtilis* ssp. *shriramensis* (MTCC-5674)cells at a concentration of $5 \times 10^5$ cfu/ml (0.5 million cells/ml of carrier) | 727 |
| | | Control | 457 |
| | | Increase over control | 37.15% |
| 3 | Tomato | 1% CMC, 2% sucrose, red polymer and *Bacillus subtilis* ssp. *shriramensis* (MTCC-5674)cells at a concentration of $5 \times 10^5$ cfu/ml (0.5 million cells/ml of carrier) | 860 |
| | | Control | 847 |
| | | Increase over control | 1.58% |

Example 7

7.1 Screening the Efficacy of Antifungal/Antimicrobial Agent to Inhibit the Growth of Human Pathogenic Fans A range of fungal species causing diseases in human beings were isolated from the people suffering from various skin and lung infections. The antifungal and/or antimicrobial activity was tested against all the isolated human pathogenic fungi.

Materials and Methods

Materials

1. *Penicillium* ssp.
2. *Aspergillus flavus*
3. *Aspergillus niger*
4. *Aspergillus nidulans*
5. PDA plates
6. Antifungal/Antimicrobial agent Isolated from *Bacillus subtilis* ssp. *shriramensis* (MTCC-5674)

Method

An aliquot of 500 µl of the culture filtrate containing antimicrobial and/or antifungal agent was added into the wells made in the PDA agar and a loop full of test fungi were inoculated at the other corner of the respective plates labeled with the respective fungus and incubated at 28° C. till the growth of fungal mycelium was observed in the vicinity of the well containing culture filtrate.

The inhibitory activity of the filtrate against the target fungus was recorded in millimetres a the inhibitory zone formed surrounding the well.

Result

A range of fungal species causing diseases in human beings were isolated from the people suffering from various skin and lung infections tested in the antimicrobial and/or antifungal assay and all of them demonstrated complete inhibition of growth in the presence of *Bacillus subtilis* ssp. *shriramensis* (MTCC-5674) culture filtrate (FIG. 24).

Conclusion

From the observations it has been concluded that the Antifungal/antimicrobial agent isolated from *Bacillus subtilis* ssp. *shriramensis* (MTCC-5674) can be used in pharmaceutical applications also.

REFERENCES

1. Compant, S., Duffy, B., Nowak, J., Clement, C. and Barka, E. A. (2005). Use of plants growth promoting bacteria for biocontrol of plant diseases: Principles, Mechanisms of action, and future prospects. Appl. Environ. Microbiol. 71:4951-4959. Sci. World J., Vol2012, pp. 001-012.
2. Hofmann, W. A. and Poorter, H. 2002. Avoiding Bias in Calculations of Relative Growth Rate. Ann. Bot., Vol. 90 (1), pp. 37-42.

3. Li, J. Yang, Q. Zhao, L-H, Zhang, S. M., Wang, Y. X. Xiao-yu and Zhao, X. Y. 2009. Purification and characterization of a novel antifungal protein from *Bacillus subtilis* strain B29. J. Zhejiang Univ. Sci. B., Vol. 10 (4) pp. 264-272.
4. Malusá, E. Sas-Paszt, L. and Ciesielaka, J. 2012.
5. Mena-Violante, H. G. and Olalde-Portugal, V. 2007. Alteration of tomato fruit quality by root inoculation with plant growth-promoting rhizobacteria (PGPR): *Bacillus subtilis* BEB-13bs. Sci. Hort., Vol. 1 (113), pp. 103-106.
6. Mohan Kumar, S. P., Chowdappa, P. and Krishna, V. (2015). Development of seed coating formulation using consortium of *Bacillus subtilis* OTPB1 and *Trichoderma harzianum* OTPB3 for plant growth promotion and induction of systemic resistance in field and horticultural crops. Indian Phytopath. 68 (1):25-31.
7. Mohiddin, F. A. and Khan, M. R. 2013. Tolerance of fungal and bacterial bio-control agents to six pesticides commonly used in the control of soil borne plant pathogens. Global J. Pests, Dis. Crop Prot., Vol. 1 (1), pp. 001-004.

RELEVANT PATENTS

1. A novel strain of *Bacillus* for controlling plant diseases and corn rootworm. (EP981540A1).
2. Strain of *Bacillus subtilis* for agricultural use. (WO2009031874A1).
3. Antifungal *Bacillus subtilis* and a microorganism wettable powder containing the same (KR2011075132A).

Annexure I

Composition of Culture Media Used
Note: A general method of media preparation is provided below. All the media compositions given below are for 100 ml volume. Compositions changes depending upon the quantity required.
(1) Preparation of T3 Broth (pH-6.8)
    Composition of T3 Medium

| S. No. | Component | Quantity |
| --- | --- | --- |
| 1 | Tryptone | 0.32% (w/v) |
| 2 | Tryptose | 0.24% (w/v) |
| 3 | Yeast Extract | 0.18% (w/v) |
| 4 | $NaH_2PO_4 \cdot H_2O$ | 0.044M |
| 5 | $Na_2HPO_4$ | 0.062M |
| 6 | $MnCl_2 \cdot 4H_2O$ | 0.0005% (w/v) |

Method
All the media components were weighed and taken in a glass bottle and dissolved in distilled water. The container with the medium was autoclaved at 1210° C. for 15 min.
(II) Preparation of T3 Agar Plates (pH-6.81)
    Composition of T3 medium

| S. No. | Component | Quantity |
| --- | --- | --- |
| 1 | Tryptone | 0.32% (w/v) |
| 2 | Tryptose | 0.24% (w/v) |
| 3 | Yeast Extract | 0.18% (w/v) |
| 4 | $NaH_2PO_4$ | 0.044M |
| 5 | $Na_2HPO_4$ | 0.062M |
| 6 | $MnCl_2$ | 0.0005% (w/v) |
| 7 | Agar agar | 2.0% (w/v) |

Method
All the media components were weighed and taken in a glass bottle and dissolved in distilled water. The glass bottle with the medium was autoclaved at 121° C. for 15 min. After autoclaving, the medium was poured in to sterile petri plates
(III) Preparation of LB broth (pH-7.0)
    Composition of LB Medium

| S. No. | Component | Quantity |
| --- | --- | --- |
| 1 | Tryptone | 1.0% (w/v) |
| 2 | Yeast Extract | 0.5% (w/v) |
| 3 | NaCl | 1.0% (w/v) |

Method
All the media components were weighed and taken in a glass bottle and dissolved in distilled water. The container with the medium was autoclaved at 121° C. for 15 min.
(IV) Preparation of LB Agar Plates (pH-7.0)
    Composition of LB Medium

| S. No. | Component | Quantity |
| --- | --- | --- |
| 1 | Tryptone | 1.0% (w/v) |
| 2 | Yeast Extract | 0.5% (w/v) |
| 3 | NaCl | 1.0% (w/v) |
| 4 | Agar agar | 2.0% (w/v) |

Method
All the media components were weighed and taken in a glass bottle and dissolved in distilled water. The glass bottle with the medium was autoclaved at 121° C. for 15 min. After autoclaving, the medium was poured in to sterile petri plates.
(V) Preparation of PDB Broth (pH-6.0)
    Composition of PDB Medium

| S. No. | Component | Quantity |
| --- | --- | --- |
| 1 | Potato Powder | 2.0% (w/v) |
| 2 | Dextrose | 2.0% (w/v) |
| 3 | Spectinomycin (Optional) | 100 µg/ml |

Method
Potato powder (2.0 g) was weighed and taken in a 250 ml glass bottle containing 50 ml of distilled water and boiled for 5 min. The boiled potato water was filtered using muslin cloth. The filtrate was collected in a fresh 250 ml glass bottle and 2.0 g of dextrose was added to it. After making the total volume to 100 ml, the bottle with the medium was autoclaved at 121° C. for 15 min.
(VI) Preparation of PDA Agar Plates (pH-6.0)
    Composition of PDA Medium

| S. No. | Component | Quantity |
| --- | --- | --- |
| 1 | Potato Powder | 2.0% (w/v) |
| 2 | Dextrose | 2.0% (w/v) |
| 3 | Agar agar | 2.0% (w/v) |
| 4 | Spectinomycin (Optional) | 100 µg/ml |

Method
Potato powder (2.0 g) was weighed and taken in a 250 ml glass bottle containing 50 ml of distilled water and boiled for 5 min. The boiled potato water was filtered using muslin cloth. The filtrate was collected in a fresh 250 ml glass bottle and 2.0 g of dextrose and 2.0 g of agar were added to it. After making the total volume to 100 ml, the bottle with the medium was autoclaved at 121° C. for 15 min. The molten PDA was poured into the sterile petri plates.

(VII) Preparation of Hugh and Leifson OF Basal Medium (OFBM) (pH-7.1)

Composition of OFBM Medium

| S. No. | Component | Quantity |
|---|---|---|
| 1 | Casein Peptone (Tryptone) 0.2% | 0.2% (w/v) |
| 2 | NaCl | 0.5% (w/v) |
| 3 | $K_2HPO_4$ | 0.03% (w/v) |
| 4 | Agar agar | 2.0% (w/v) |
| 5 | Bromothymol Blue | 0.004% (w/v) |

Method

All the media components were weighed and taken in a glass bottle and dissolved in distilled water. The glass bottle with the medium was autoclaved at 121° C. for 15 min. After autoclaving, the medium was poured in to sterile culture tubes.

(VI) Preparation of SIM (Sulphide Indole Motility) Medium (pH-7.3)

Composition of SIM Medium

| S. No. | Component | Quantity |
|---|---|---|
| 1 | Peptone | 3.0% (w/v) |
| 2 | Beef Extract | 0.3% (w/v) |
| 3 | Ferrous Ammonium Sulphate | 0.02% (w/v) |
| 4 | Sodium thiosulhphate | 0.0025% (w/v) |
| 7 | Agar agar | 2.0% (w/v) |

Method

All the media components were weighed and taken in a glass bottle and dissolved in distilled water. The glass bottle with the medium was autoclaved at 121° C. for 15 min. After autoclaving, the medium of molten stage was poured in to sterile culture tubes.

Annexure II

Preparation Phosphate Buffer

| S. No. | Component | Quantity | Weight for 100 ml |
|---|---|---|---|
| 4 | $NaH_2PO_4 \cdot H_2O$ | 1M | 5.38 g |
| 5 | $Na_2HPO_4$ | 1M | 8.66 g |
| | pH | | 7.0 |

Method

Both the phosphate salts were taken in a glass beaker, 50 ml distilled water was added to salts and stirred on a magnetic stirrer using a magnetic bar. After ensuring that the phosphate salts are completely dissolved, the solution was made up to 100 ml with distilled water.

Annexure III

Carriers and Other Agents Used in the Experiment

| S. No. | Agent Name | Composition | Used as/for | Make |
|---|---|---|---|---|
| 1 | CMC | Carboxy Methyl Cellulose | Binding agent | Himedia |
| 2 | Carbendazim | Carbendazim WP50 | fungicide | Bavistin |
| 3 | Soilrite | Perlite + Peat Moss + Vermiculite | Fungus multiplication | KEL (Keltech Energies Ltd) |

ABBREVIATIONS

| S. No. | Short Form | Full Form |
|---|---|---|
| 1 | ATCC | American Type Culture Collection |
| 2 | CMC | Carboxy Methyl Cellulose |
| 3 | CFU | Colony Forming Units |
| 4 | L | Liter |
| 5 | LB | Luria-Bertani |
| 6 | µl | Micro Liter |
| 7 | MTCC | Microbial Type Culture Collection |
| 8 | Ml | Milli Liter |
| 9 | MIC | Minimal Inhibitory Concentration |
| 10 | Min | Minutes |
| 11 | M | Molar |
| 12 | NFCCI | National Fungal Culture Collection of India |
| 13 | OFBM | Oxidation Fermentation Basal Medium |
| 14 | PDA | Potato Dextrose Agar |
| 15 | PDB | Potato Dextrose Broth |
| 16 | RPM | Revolutions Per Minute |
| 17 | Ssp | Sub-species |
| 18 | SIM | Sulphide Indole Motility |
| 19 | v/v | Volume by volume |
| 20 | w/v | Weight by volume |
| 21 | w/w | Weight by weight |
| 22 | WP | Wettable Powder |

We claim:

1. A composition comprising an extract of a bacterium belonging to *Bacillus subtilis* ssp. *shriramensis* having the accession number MTCC-5674 and one or more antimicrobial, antifungal or plant growth promoting agents, wherein the composition exhibits antimicrobial or antifungal activity.

2. The composition of claim 1, wherein the process of its production comprises:
   a) growing *Bacillus subtilis* ssp. *shriramensis* having the accession number MTCC-5674 in a T3medium having pH 6.8 in a shaking incubator at 3020 C. for 60 h; and
   b) recovering the extract having antimicrobial or antifungal activity.

3. The composition of claim 1, wherein the extract is from a *Bacillus subtilis* ssp. *shriramensis* grown under aerobic conditions.

4. The composition of claim 1 wherein the composition comprises a concentrated extract.

5. A composition comprising a bacterium belonging to *Bacillus subtilis* ssp. *shriramensis* having the accession number MTCC-5674 and one or more antimicrobial, antifungal or plant growth promoting agents, wherein the composition has antimicrobial or antifungal and plant growth promoting activity at a concentration $5 \times 10^5$ cfu/ml to $5 \times 10^7$ cfu/ml of the bacterium.

6. The composition of claim 1, wherein the composition has antimicrobial or antifungal activity at a concentration of 4 µg/µl to 20 µg/µl of the extract.

7. A composition comprising a bacterium belonging to *Bacillus subtilis* ssp. *shriramensis* having the accession number MTCC-5674, exhibiting antimicrobial or antifungal and plant growth promoting activity, an extract therefrom exhibiting antimicrobial or antifungal activity, and one or more antimicrobial, antifungal or plant growth promoting agents, wherein the composition has antimicrobial or antifungal and plant growth promoting activity.

8. The composition of claim 7 further comprising an agriculturally acceptable carrier.

9. The composition of claim 5 further comprising an agriculturally acceptable carrier.

10. The composition of claim 6 further comprising an agriculturally acceptable carrier.

11. A method for inhibiting growth of pathogenic fungi and/or bacteria, wherein said method comprises contacting the pathogenic fungi and/or bacteria with an effective amount of $5 \times 10^5$ cfu/ml to $5 \times 10^7$ cfu/ml of a bacterium belonging to *Bacillus subtilis* ssp. *shriramensis* having the accession number MTCC-5674, exhibiting antimicrobial or antifungal and plant growth promoting activity or a composition comprising a bacterium belonging to *Bacillus subtilis* ssp. *shriramensis* having the accession number MTCC-5674, exhibiting antimicrobial or antifungal and plant growth promoting activity or an extract therefrom exhibiting antimicrobial or antifungal activity, wherein the composition has antimicrobial or antifungal and plant growth promoting activity.

12. The method of claim 11 wherein the composition further comprises one or more antimicrobial, antifungal or plant growth promoting agents.

13. The method of claim 11 wherein the composition further comprises an agriculturally acceptable carrier.

* * * * *

UNITED STATES PATENT AND TRADEMARK OFFICE
CERTIFICATE OF CORRECTION

PATENT NO. : 10,327,448 B2
APPLICATION NO. : 15/503941
DATED : June 25, 2019
INVENTOR(S) : Santosh Kumar Dodda, Dwarkesh Singh Parihar and Paresh Kumar Verma Page 1 of 1

It is certified that error appears in the above-identified patent and that said Letters Patent is hereby corrected as shown below:

In the Claims

Claim 2, Column 38, Line 52, delete "T3medium" and insert --T3 medium--.

Claim 2, Column 38, Line 53, delete "3020 C." and insert --30°C.--.

Signed and Sealed this
Third Day of September, 2019

Andrei Iancu
*Director of the United States Patent and Trademark Office*